(12) United States Patent
Thuot Rann et al.

(10) Patent No.: US 7,281,811 B2
(45) Date of Patent: Oct. 16, 2007

(54) MULTI-CLARITY LENSES

(75) Inventors: Raechell Maria Thuot Rann, Racine, WI (US); Imre J. Dancs, Greenfield, WI (US); John S. Trent, Franklin, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 114 days.

(21) Appl. No.: 11/097,770

(22) Filed: Mar. 31, 2005

(65) Prior Publication Data

US 2006/0221594 A1 Oct. 5, 2006

(51) Int. Cl.
*F21V 33/00* (2006.01)
*F24F 6/08* (2006.01)

(52) U.S. Cl. .......................... 362/96; 362/92; 362/253; 362/268; 219/220; 392/395

(58) Field of Classification Search ................... 362/96, 362/332, 253, 311, 641–643, 92, 234, 800, 362/161, 240, 242, 268; 126/213, 209; 219/758, 220, 230, 201, 209; 392/394–395, 392/393
See application file for complete search history.

(56) References Cited

U.S. PATENT DOCUMENTS

| | | |
|---|---|---|
| 38,150 A | 4/1863 | Colburn |
| 446,953 A | 2/1891 | Robert |
| 514,422 A | 2/1894 | Kellogg |
| 554,115 A | 2/1896 | Fisher |
| 699,652 A | 5/1902 | Campbell et al. |
| 1,178,575 A | 4/1916 | Collins |
| 1,403,548 A | 1/1922 | Gudeman |
| 1,712,204 A | 5/1929 | Gibney |
| 1,751,257 A | 3/1930 | Vallebuona et al. |
| 1,800,156 A | 4/1931 | Rotheim |
| 1,977,997 A | 10/1934 | Patterson et al. |
| 1,981,650 A | 11/1934 | Larsen |
| 1,994,932 A | 3/1935 | Vidal |
| 2,192,019 A | 2/1940 | Schepmoes |
| 2,230,265 A | 2/1941 | Robinson |
| 2,372,371 A | 3/1945 | Eisner |
| 2,424,268 A | 7/1947 | Delane et al. |

(Continued)

FOREIGN PATENT DOCUMENTS

EP      0 252 642      1/1988

(Continued)

OTHER PUBLICATIONS

International Search Report and Written Opinion dated Aug. 1, 2006, Appl. No. PCT/US/2006/011900.

(Continued)

*Primary Examiner*—Ali Alavi
*Assistant Examiner*—Bao Q. Truong

(57) ABSTRACT

The present invention is directed toward apparatuses, devices, methods, kits, programs, and combinations to disperse and/or project light. For example, in one embodiment of the present invention where a light effect of glowing, diffuse, and projected light is desired, one lens is provided that diffuses light in one section of the lens and is substantially clear in another section to allow substantially all the light to pass through the lens. In other embodiments to obtain the same effect, one or more lenses diffuse light while one or more other lenses are clear to allow substantially all the light to pass through the lens.

20 Claims, 16 Drawing Sheets

U.S. PATENT DOCUMENTS

| | | |
|---|---|---|
| 2,435,756 A | 2/1948 | Schlesinger |
| 2,469,656 A | 5/1949 | Lienert |
| 2,557,501 A | 6/1951 | Fusay et al. |
| 2,591,818 A | 4/1952 | Huff |
| 2,597,195 A | 5/1952 | Smith |
| 2,668,993 A | 2/1954 | Bair |
| 2,931,880 A | 4/1960 | Yaffe |
| 2,942,090 A | 6/1960 | Diehl |
| 3,248,530 A | 4/1966 | Titmas |
| 3,358,552 A | 12/1967 | Schneider |
| 3,373,341 A | 3/1968 | Wattson |
| 3,386,005 A | 5/1968 | Roland et al. |
| 3,436,310 A | 4/1969 | Arnold et al. |
| 3,443,083 A | 5/1969 | Curran |
| 3,543,122 A | 11/1970 | Klebanoff et al. |
| 3,545,650 A | 12/1970 | Williams |
| 3,588,859 A | 6/1971 | Petree |
| 3,615,041 A | 10/1971 | Bischoff |
| 3,747,902 A | 7/1973 | Bailey |
| 3,780,260 A | 12/1973 | Elsner |
| 3,790,772 A | 2/1974 | Newman et al. |
| 3,864,080 A | 2/1975 | Valbona et al. |
| 3,872,280 A | 3/1975 | Van Dalen |
| 3,948,445 A | 4/1976 | Andeweg |
| 4,084,079 A | 4/1978 | Costello |
| 4,106,671 A | 8/1978 | Sharples |
| 4,166,293 A | 9/1979 | Anis |
| 4,184,612 A | 1/1980 | Freyre |
| 4,197,671 A | 4/1980 | De Brouwer |
| 4,202,387 A | 5/1980 | Upton |
| 4,217,315 A | 8/1980 | Keeler, II |
| 4,229,415 A | 10/1980 | Bryson |
| 4,244,525 A | 1/1981 | Manna |
| 4,250,537 A | 2/1981 | Roegner et al. |
| 4,285,028 A | 8/1981 | Sundin et al. |
| 4,301,095 A | 11/1981 | Mettler et al. |
| 4,315,665 A | 2/1982 | Haines |
| 4,338,547 A | 7/1982 | McCaslin |
| 4,346,059 A | 8/1982 | Spector |
| 4,391,781 A | 7/1983 | van Lit |
| 4,415,797 A | 11/1983 | Choustoulakis |
| 4,432,938 A | 2/1984 | Meetze, Jr. |
| 4,435,732 A | 3/1984 | Hyatt |
| 4,493,011 A | 1/1985 | Spector |
| 4,549,250 A | 10/1985 | Spector |
| 4,571,485 A | 2/1986 | Spector |
| 4,583,686 A | 4/1986 | Martens et al. |
| 4,597,781 A | 7/1986 | Spector |
| 4,609,978 A | 9/1986 | Hsieh et al. |
| 4,611,266 A | 9/1986 | Schwartz |
| 4,666,638 A | 5/1987 | Baker et al. |
| 4,670,820 A | 6/1987 | Eddins et al. |
| 4,689,515 A | 8/1987 | Benndorf et al. |
| 4,702,418 A | 10/1987 | Carter et al. |
| 4,703,155 A | 10/1987 | Suhajda |
| 4,703,314 A | 10/1987 | Spani |
| 4,707,338 A | 11/1987 | Spector |
| 4,714,984 A | 12/1987 | Spector |
| 4,715,702 A | 12/1987 | Dillon |
| 4,739,928 A | 4/1988 | O'Neil |
| 4,750,471 A | 6/1988 | Hautmann et al. |
| 4,795,883 A | 1/1989 | Glucksman et al. |
| 4,816,973 A | 3/1989 | Atalla et al. |
| 4,830,791 A | 5/1989 | Muderlak et al. |
| 4,837,421 A | 6/1989 | Luthy |
| 4,840,444 A | 6/1989 | Hewitt |
| 4,844,050 A | 7/1989 | Hautmann et al. |
| 4,849,606 A | 7/1989 | Martens, III et al. |
| 4,856,103 A | 8/1989 | Compton |
| 4,858,079 A | 8/1989 | Ohashi |
| 4,866,580 A | 9/1989 | Blackerby |
| 4,870,551 A | 9/1989 | Nagel |
| 4,873,029 A | 10/1989 | Blum |
| 4,934,792 A | 6/1990 | Tovi |
| 4,955,714 A | 9/1990 | Stotler et al. |
| 4,968,487 A | 11/1990 | Yamamoto et al. |
| 5,017,909 A | 5/1991 | Goekler |
| 5,038,394 A | 8/1991 | Hasegawa et al. |
| 5,055,822 A | 10/1991 | Campbell et al. |
| 5,095,647 A | 3/1992 | Zobele et al. |
| 5,111,477 A | 5/1992 | Muderlak |
| 5,115,975 A | 5/1992 | Shilling |
| 5,118,319 A | 6/1992 | Smith et al. |
| 5,135,485 A | 8/1992 | Cohen et al. |
| 5,136,483 A | 8/1992 | Schoniger et al. |
| 5,147,585 A | 9/1992 | Blum |
| 5,175,791 A | 12/1992 | Muderlak et al. |
| 5,201,025 A | 4/1993 | Landesberg |
| 5,213,523 A | 5/1993 | Hygema et al. |
| 5,214,458 A | 5/1993 | Kanai |
| 5,222,186 A | 6/1993 | Schimanski et al. |
| 5,230,837 A | 7/1993 | Babasade |
| 5,233,375 A | 8/1993 | Williams et al. |
| 5,260,919 A | 11/1993 | Tsai |
| 5,274,215 A | 12/1993 | Jackson |
| 5,283,601 A | 2/1994 | Lowe |
| 5,283,723 A | 2/1994 | Wu |
| 5,309,185 A | 5/1994 | Harper |
| 5,309,338 A | 5/1994 | Liu |
| 5,324,490 A | 6/1994 | Van Vlahakis |
| D350,209 S | 8/1994 | Martin |
| 5,370,829 A | 12/1994 | Kunze |
| 5,382,410 A | 1/1995 | Peltier |
| D357,330 S | 4/1995 | Wong et al. |
| 5,419,879 A | 5/1995 | Vlahakis et al. |
| 5,432,623 A | 7/1995 | Egan et al. |
| 5,449,117 A | 9/1995 | Muderlak et al. |
| 5,452,270 A | 9/1995 | Ikeda et al. |
| 5,464,710 A | 11/1995 | Yang |
| 5,483,689 A | 1/1996 | O'Donnell, Jr. et al. |
| 5,484,086 A | 1/1996 | Pu |
| 5,485,308 A | 1/1996 | Hirata et al. |
| 5,497,102 A | 3/1996 | Burrows et al. |
| 5,498,397 A | 3/1996 | Horng |
| 5,512,371 A | 4/1996 | Gupta et al. |
| 5,517,264 A | 5/1996 | Sutton |
| 5,521,357 A | 5/1996 | Lock et al. |
| 5,524,101 A | 6/1996 | Thorgersen et al. |
| D372,769 S | 8/1996 | Ganor |
| 5,544,812 A | 8/1996 | Torres |
| 5,549,247 A | 8/1996 | Rossman et al. |
| 5,556,192 A | 9/1996 | Wang |
| 5,591,409 A | 1/1997 | Watkins |
| 5,616,172 A | 4/1997 | Tuckerman et al. |
| 5,633,623 A | 5/1997 | Campman |
| D381,443 S | 7/1997 | Yuen |
| D381,444 S | 7/1997 | Yuen |
| 5,647,053 A | 7/1997 | Schroeder et al. |
| 5,662,835 A | 9/1997 | Collingwood |
| 5,673,825 A | 10/1997 | Chen |
| 5,690,509 A | 11/1997 | Eisenbraun |
| D386,974 S | 12/1997 | Wefler |
| 5,716,119 A | 2/1998 | Patel |
| D393,063 S | 3/1998 | Wefler |
| 5,752,766 A | 5/1998 | Bailey et al. |
| 5,757,111 A | 5/1998 | Sato |
| 5,757,459 A | 5/1998 | Bhalakia et al. |
| D395,529 S | 6/1998 | Yuen |
| 5,763,080 A | 6/1998 | Stahl et al. |
| 5,772,074 A | 6/1998 | Dial et al. |
| 5,788,931 A | 8/1998 | Munoz Quintana |
| 5,830,578 A | 11/1998 | Ono et al. |
| 5,852,946 A | 12/1998 | Cowger |
| 5,863,108 A | 1/1999 | Lederer |

| | | | | | | |
|---|---|---|---|---|---|---|
| 5,871,153 A | 2/1999 | Doggett, Jr. | | 6,392,549 B1 | 5/2002 | Wu |
| 5,875,968 A | 3/1999 | Miller et al. | | D458,395 S | 6/2002 | Piepgras |
| 5,876,678 A | 3/1999 | Harrell et al. | | 6,398,381 B1 | 6/2002 | Tseng |
| 5,903,710 A | 5/1999 | Wefler et al. | | D460,544 S | 7/2002 | Garcia |
| 5,909,845 A | 6/1999 | Greatbatch et al. | | D460,573 S | 7/2002 | Gee, II |
| 5,922,231 A | 7/1999 | Karst et al. | | 6,420,877 B1 | 7/2002 | Replogle |
| 5,924,784 A | 7/1999 | Chliwnyj et al. | | 6,423,892 B1 | 7/2002 | Ramaswamy |
| D412,569 S | 8/1999 | Muller | | D461,549 S | 8/2002 | Garcia |
| 5,937,140 A | 8/1999 | Leonard et al. | | D461,885 S | 8/2002 | Jordi |
| 5,940,577 A | 8/1999 | Steinel | | 6,431,719 B1 | 8/2002 | Lau et al. |
| 5,945,094 A | 8/1999 | Martin et al. | | 6,439,471 B2 | 8/2002 | Ehrlich et al. |
| 5,964,519 A | 10/1999 | Chun-Ying | | D462,755 S | 9/2002 | Millan |
| 5,976,503 A | 11/1999 | Martin et al. | | D463,610 S | 9/2002 | Piepgras |
| 5,980,064 A | 11/1999 | Metroyanis | | 6,446,880 B1 | 9/2002 | Schram et al. |
| 6,016,038 A | 1/2000 | Mueller et al. | | D464,416 S | 10/2002 | von Dohlen et al. |
| 6,020,983 A | 2/2000 | Neu et al. | | 6,457,826 B1 | 10/2002 | Lett |
| 6,039,899 A | 3/2000 | Martin et al. | | 6,459,919 B1 | 10/2002 | Lys et al. |
| 6,044,202 A | 3/2000 | Junkel | | 6,466,739 B2 | 10/2002 | Ambrosi et al. |
| 6,072,606 A | 6/2000 | Huether et al. | | 6,478,440 B1 | 11/2002 | Jaworski et al. |
| 6,097,881 A | 8/2000 | DeWitt et al. | | 6,479,594 B1 | 11/2002 | Cheung et al. |
| 6,101,038 A | 8/2000 | Hebert et al. | | 6,482,863 B2 | 11/2002 | Munagavalasa et al. |
| 6,104,866 A | 8/2000 | DeWitt et al. | | D468,033 S | 12/2002 | Warren et al. |
| 6,104,867 A | 8/2000 | Stathakis et al. | | D468,035 S | 12/2002 | Blanc et al. |
| 6,123,935 A | 9/2000 | Wefler et al. | | 6,503,459 B1 | 1/2003 | Leonard et al. |
| 6,135,369 A | 10/2000 | Prendergast et al. | | D469,862 S | 2/2003 | Cruver, IV et al. |
| D433,521 S | 11/2000 | Jaworski | | 6,528,954 B1 | 3/2003 | Lys et al. |
| D433,744 S | 11/2000 | Basaganas | | 6,536,746 B2 | 3/2003 | Watkins |
| 6,142,653 A | 11/2000 | Larson | | D473,638 S | 4/2003 | Cruver, IV |
| 6,145,241 A | 11/2000 | Okuno | | 6,547,553 B2 | 4/2003 | Koch et al. |
| 6,149,283 A | 11/2000 | Conway et al. | | 6,548,967 B1 | 4/2003 | Dowling et al. |
| 6,150,774 A | 11/2000 | Mueller et al. | | 6,554,203 B2 | 4/2003 | Hess et al. |
| 6,150,943 A | 11/2000 | Lehman et al. | | 6,557,998 B2 | 5/2003 | Portney |
| 6,151,827 A | 11/2000 | Smith et al. | | 6,558,022 B2 | 5/2003 | Kawahara |
| 6,153,703 A | 11/2000 | Lustiger et al. | | 6,567,613 B2 | 5/2003 | Rymer |
| 6,154,607 A | 11/2000 | Flashinski et al. | | 6,569,387 B1 | 5/2003 | Furner et al. |
| D434,842 S | 12/2000 | Thomas et al. | | D475,446 S | 6/2003 | Millan |
| 6,163,098 A | 12/2000 | Taylor et al. | | 6,575,610 B2 | 6/2003 | Natsume |
| 6,166,496 A | 12/2000 | Lys et al. | | 6,577,080 B2 | 6/2003 | Lys et al. |
| D436,657 S | 1/2001 | Heatter | | 6,581,915 B2 | 6/2003 | Bartsch et al. |
| D437,069 S | 1/2001 | Allison | | 6,584,986 B2 | 7/2003 | Gindi |
| D437,636 S | 2/2001 | Basaganas | | 6,588,435 B1 | 7/2003 | Gindi |
| 6,191,826 B1 | 2/2001 | Murakami et al. | | 6,602,475 B1 | 8/2003 | Chiao |
| 6,196,471 B1 | 3/2001 | Ruthenberg | | 6,606,548 B2 | 8/2003 | Ambrosi et al. |
| 6,199,983 B1 | 3/2001 | Kato et al. | | 6,608,453 B2 | 8/2003 | Morgan et al. |
| 6,211,626 B1 | 4/2001 | Lys et al. | | 6,611,297 B1 | 8/2003 | Akashi et al. |
| 6,216,925 B1 | 4/2001 | Garon | | 6,619,559 B2 | 9/2003 | Wohrle |
| 6,236,807 B1 | 5/2001 | Ruffolo et al. | | 6,622,662 B1 | 9/2003 | Wolpert et al. |
| 6,239,216 B1 | 5/2001 | Montanari et al. | | 6,624,597 B2 | 9/2003 | Dowling et al. |
| 6,241,362 B1 | 6/2001 | Morrison | | D480,792 S | 10/2003 | Millan |
| 6,254,065 B1 | 7/2001 | Ehrensperger et al. | | 6,631,888 B1 | 10/2003 | Prueter |
| 6,267,297 B1 | 7/2001 | Contadini et al. | | D481,787 S | 11/2003 | Millan |
| 6,268,062 B1 | 7/2001 | DeMeuse | | 6,644,507 B2 | 11/2003 | Borut et al. |
| 6,270,720 B1 | 8/2001 | Mandish | | D483,104 S | 12/2003 | Hill et al. |
| 6,275,651 B1 | 8/2001 | Voit | | 6,661,967 B2 | 12/2003 | Levine et al. |
| 6,278,840 B1 | 8/2001 | Basaganas Millan | | 6,667,576 B1 | 12/2003 | Westhoff |
| 6,281,867 B2 | 8/2001 | Kurematsu et al. | | 6,676,284 B1 | 1/2004 | Wynne Willson |
| 6,292,196 B1 | 9/2001 | Fukunaga et al. | | 6,682,331 B1 | 1/2004 | Peh et al. |
| 6,292,305 B1 | 9/2001 | Sakuma et al. | | 6,685,339 B2 | 2/2004 | Daughtry et al. |
| 6,292,901 B1 | 9/2001 | Lys et al. | | 6,685,343 B2 | 2/2004 | Mabuchi |
| 6,302,559 B1 | 10/2001 | Warren | | 6,688,752 B2 | 2/2004 | Moore |
| 6,337,080 B1 | 1/2002 | Fryan et al. | | 6,690,120 B2 | 2/2004 | Oskorep et al. |
| 6,340,868 B1 | 1/2002 | Lys et al. | | 6,697,571 B2 | 2/2004 | Triplett et al. |
| 6,341,732 B1 | 1/2002 | Martin et al. | | 6,698,665 B2 | 3/2004 | Minamite et al. |
| D453,562 S | 2/2002 | Makino | | 6,709,126 B1 * | 3/2004 | Leen ........................ 362/95 |
| 6,350,417 B1 | 2/2002 | Lau et al. | | 6,713,024 B1 | 3/2004 | Arnell et al. |
| 6,361,752 B1 | 3/2002 | Demarest et al. | | 6,714,725 B2 | 3/2004 | Grone et al. |
| D455,486 S | 4/2002 | Makino | | 6,717,376 B2 | 4/2004 | Lys et al. |
| 6,368,564 B1 | 4/2002 | Smith | | 6,719,217 B1 | 4/2004 | Tawara et al. |
| 6,377,164 B1 | 4/2002 | Fulmer | | 6,720,745 B2 | 4/2004 | Lys et al. |
| D457,667 S | 5/2002 | Piepgras | | 6,721,102 B2 | 4/2004 | Bourdelais et al. |
| D457,669 S | 5/2002 | Piepgras | | 6,727,332 B2 | 4/2004 | Demain |
| D457,974 S | 5/2002 | Piepgras | | 6,729,552 B1 | 5/2004 | McEwen |
| 6,390,453 B1 | 5/2002 | Frederickson et al. | | 6,729,746 B2 | 5/2004 | Suehiro et al. |

| | | | | | |
|---|---|---|---|---|---|
| 6,733,719 B2 | 5/2004 | DiNardo et al. | 6,950,607 B2 | 9/2005 | Yip et al. |
| 6,733,898 B2 | 5/2004 | Kim et al. | 6,953,260 B1 | 10/2005 | Allen |
| D491,678 S | 6/2004 | Piepgras | 6,953,265 B2 | 10/2005 | Suehiro et al. |
| D492,042 S | 6/2004 | Piepgras | 6,955,581 B1 | 10/2005 | Liu |
| 6,752,327 B2 | 6/2004 | Martens, III et al. | 6,957,012 B2 | 10/2005 | He et al. |
| 6,758,566 B2 | 7/2004 | Goulden et al. | 6,965,205 B2 | 11/2005 | Piepgras et al. |
| 6,759,961 B2 | 7/2004 | Fitzgerald et al. | 6,967,448 B2 | 11/2005 | Morgan et al. |
| 6,763,624 B2 | 7/2004 | Gow | 6,969,954 B2 | 11/2005 | Lys |
| 6,766,773 B2 | 7/2004 | Wolpert et al. | 6,975,079 B2 | 12/2005 | Lys et al. |
| 6,768,865 B2 | 7/2004 | Stathakis et al. | 2001/0011779 A1 | 8/2001 | Stover |
| 6,774,584 B2 | 8/2004 | Lys et al. | 2001/0032655 A1 | 10/2001 | Gindi |
| 6,775,470 B2 | 8/2004 | Zobele et al. | 2002/0021892 A1 | 2/2002 | Ambrosi et al. |
| 6,777,891 B2 | 8/2004 | Lys et al. | 2002/0036617 A1 | 3/2002 | Pryor |
| 6,779,905 B1 | 8/2004 | Mazursky et al. | 2002/0048169 A1 | 4/2002 | Dowling et al. |
| 6,781,329 B2 | 8/2004 | Mueller et al. | 2002/0066798 A1 | 6/2002 | Laudamiel-Pellet et al. |
| 6,782,194 B2 | 8/2004 | Schneiderbauer | 2002/0068009 A1 | 6/2002 | Laudamiel-Pellet et al. |
| 6,783,117 B2 | 8/2004 | Wohrle | 2002/0068010 A1 | 6/2002 | Laudamiel-Pellet et al. |
| 6,788,011 B2 | 9/2004 | Mueller et al. | 2002/0075677 A1 | 6/2002 | Dokupll |
| 6,792,199 B2 | 9/2004 | Levine et al. | 2002/0097978 A1 | 7/2002 | Lowry et al. |
| 6,801,003 B2 | 10/2004 | Schanberger et al. | 2002/0113555 A1 | 8/2002 | Lys et al. |
| 6,802,460 B2 | 10/2004 | Hess et al. | 2002/0113912 A1 | 8/2002 | Wright et al. |
| 6,806,659 B1 | 10/2004 | Mueller et al. | 2002/0136542 A1 | 9/2002 | He et al. |
| 6,810,204 B2 | 10/2004 | Grone et al. | 2002/0136886 A1 | 9/2002 | He et al. |
| 6,811,287 B2 | 11/2004 | Roller et al. | 2002/0145394 A1 | 10/2002 | Morgan et al. |
| 6,813,094 B2 | 11/2004 | Kaminsky et al. | 2002/0159274 A1 | 10/2002 | Hubbell et al. |
| 6,819,506 B1 | 11/2004 | Taylor et al. | 2002/0172512 A1 | 11/2002 | Stathakis et al. |
| 6,824,296 B2 | 11/2004 | Souza et al. | 2002/0195975 A1 | 12/2002 | Schanberger et al. |
| 6,827,286 B2 | 12/2004 | Zobele | 2003/0012018 A1 | 1/2003 | Kluth |
| 6,827,466 B2 | 12/2004 | Tsai | 2003/0028260 A1 | 2/2003 | Blackwell |
| 6,829,852 B1 | 12/2004 | Uehran | 2003/0028888 A1 | 2/2003 | Hunter et al. |
| 6,832,794 B2 | 12/2004 | He et al. | 2003/0035917 A1 | 2/2003 | Hyman |
| 6,837,585 B2 | 1/2005 | Roggatz | 2003/0057887 A1 | 3/2003 | Dowling et al. |
| 6,839,506 B2 | 1/2005 | He et al. | 2003/0063902 A1 | 4/2003 | Pedrotti et al. |
| 6,843,965 B2 | 1/2005 | Matulevich | 2003/0076281 A1 | 4/2003 | Morgan |
| 6,843,969 B1 | 1/2005 | Anno | 2003/0137258 A1 | 7/2003 | Piepgras et al. |
| 6,846,098 B2 | 1/2005 | Bourdelais et al. | 2003/0138241 A1 | 7/2003 | Pedrotti et al. |
| 6,848,795 B2 | 2/2005 | Kaminsky et al. | 2003/0147243 A1 | 8/2003 | Alduby |
| 6,850,697 B2 | 2/2005 | Basaganas Millan | 2003/0168524 A1 | 9/2003 | Hess et al. |
| 6,854,717 B2 | 2/2005 | Millan | 2003/0168751 A1 | 9/2003 | Bartsch et al. |
| 6,857,579 B2 | 2/2005 | Harris | 2003/0169400 A1 | 9/2003 | Buazza et al. |
| D502,540 S | 3/2005 | Cruver, IV et al. | 2003/0169513 A1 | 9/2003 | Kaminsky et al. |
| 6,862,402 B2 | 3/2005 | Kim | 2003/0169514 A1 | 9/2003 | Bourdelais et al. |
| 6,862,403 B2 * | 3/2005 | Pedrotti et al. ............ 392/395 | 2003/0175019 A1 | 9/2003 | Bresolin et al. |
| 6,864,110 B2 | 3/2005 | Summers et al. | 2003/0175148 A1 | 9/2003 | Kvietok et al. |
| 6,869,204 B2 | 3/2005 | Morgan et al. | 2003/0194355 A1 | 10/2003 | Pedrotti et al. |
| 6,871,794 B2 | 3/2005 | McEwen | 2003/0205364 A1 | 11/2003 | Sauciuc et al. |
| 6,871,982 B2 | 3/2005 | Homan et al. | 2003/0206411 A9 | 11/2003 | Dowling et al. |
| D504,171 S | 4/2005 | Ibarra et al. | 2003/0214080 A1 | 11/2003 | Maki et al. |
| 6,883,929 B2 | 4/2005 | Dowling | 2003/0222587 A1 | 12/2003 | Dowling et al. |
| 6,885,811 B2 | 4/2005 | He et al. | 2004/0004839 A1 | 1/2004 | Souza et al. |
| 6,888,322 B2 | 5/2005 | Dowling et al. | 2004/0007710 A1 | 1/2004 | Roy et al. |
| 6,889,003 B2 | 5/2005 | Triplett et al. | 2004/0007787 A1 | 1/2004 | Kvietok et al. |
| 6,890,642 B2 | 5/2005 | Kaminsky et al. | 2004/0009103 A1 | 1/2004 | Westring |
| 6,895,177 B2 | 5/2005 | He et al. | 2004/0016818 A1 | 1/2004 | Murdell et al. |
| 6,897,381 B2 | 5/2005 | He et al. | 2004/0028551 A1 | 2/2004 | Kvietok et al. |
| 6,897,624 B2 | 5/2005 | Lys et al. | 2004/0033067 A1 | 2/2004 | He et al. |
| 6,899,280 B2 | 5/2005 | Kotary et al. | 2004/0033171 A1 | 2/2004 | Kveitok et al. |
| 6,901,215 B2 | 5/2005 | He et al. | 2004/0035409 A1 | 2/2004 | Harwig et al. |
| 6,901,925 B2 | 6/2005 | Coughlin | 2004/0036006 A1 | 2/2004 | Dowling |
| 6,909,840 B2 | 6/2005 | Harwig et al. | 2004/0044106 A1 | 3/2004 | Portnoy et al. |
| 6,917,402 B2 | 7/2005 | Hosoda et al. | 2004/0076410 A1 | 4/2004 | Zobele et al. |
| 6,917,754 B2 * | 7/2005 | Pedrotti et al. ............ 392/395 | 2004/0090191 A1 | 5/2004 | Mueller et al. |
| 6,920,282 B2 | 7/2005 | He et al. | 2004/0090787 A1 | 5/2004 | Dowling et al. |
| D508,558 S | 8/2005 | Wolpert et al. | 2004/0095746 A1 | 5/2004 | Murphy |
| 6,923,383 B1 | 8/2005 | Joshi | 2004/0105261 A1 | 6/2004 | Ducharme |
| 6,924,233 B1 | 8/2005 | Chua et al. | 2004/0105264 A1 | 6/2004 | Spero |
| 6,926,435 B2 | 8/2005 | Li | 2004/0105669 A1 | 6/2004 | He et al. |
| 6,931,202 B2 | 8/2005 | Pedrotti et al. | 2004/0113568 A1 | 6/2004 | Dowling et al. |
| 6,933,680 B2 | 8/2005 | Oskorep et al. | 2004/0130909 A1 | 7/2004 | Mueller et al. |
| 6,936,978 B2 | 8/2005 | Morgan et al. | 2004/0131509 A1 | 7/2004 | He et al. |
| 6,938,883 B2 | 9/2005 | Adams et al. | 2004/0141315 A1 | 7/2004 | Sherburne |
| 6,945,468 B1 | 9/2005 | Rodriguez et al. | 2004/0141321 A1 | 7/2004 | Dowling et al. |
| 6,946,805 B2 | 9/2005 | Segan et al. | 2004/0144884 A1 | 7/2004 | He et al. |

| | | | | | | |
|---|---|---|---|---|---|---|
| 2004/0145067 A1 | 7/2004 | Millan | | 2005/0218870 A1 | 10/2005 | Lys et al. |
| 2004/0150993 A1 | 8/2004 | McElhaney et al. | | 2005/0219838 A1 | 10/2005 | Belliveau |
| 2004/0150994 A1 | 8/2004 | Kazar et al. | | 2005/0219872 A1 | 10/2005 | Lys et al. |
| 2004/0155609 A1 | 8/2004 | Lys et al. | | 2005/0225856 A1 | 10/2005 | Kokuzawa et al. |
| 2004/0160199 A1 | 8/2004 | Morgan et al. | | 2005/0226788 A1 | 10/2005 | Hrybyk et al. |
| 2004/0178751 A1 | 9/2004 | Mueller et al. | | 2005/0231133 A1 | 10/2005 | Lys et al. |
| 2004/0179167 A1 | 9/2004 | Dahi et al. | | 2005/0232831 A1 | 10/2005 | Taylor et al. |
| 2004/0208675 A1 | 10/2004 | Horikoshi et al. | | 2005/0236029 A1 | 10/2005 | Dowling |
| 2004/0212993 A1 | 10/2004 | Morgan et al. | | 2005/0236998 A1 | 10/2005 | Mueller et al. |
| 2004/0240890 A1 | 12/2004 | Lys et al. | | 2005/0248299 A1 | 11/2005 | Chemel et al. |
| 2004/0247300 A1 | 12/2004 | He et al. | | 2005/0253533 A1 | 11/2005 | Lys et al. |
| 2004/0249094 A1 | 12/2004 | Demain | | 2005/0275626 A1 | 12/2005 | Mueller et al. |
| 2004/0257007 A1 | 12/2004 | Lys et al. | | 2005/0276053 A1 | 12/2005 | Nortrup |
| 2005/0002105 A1 | 1/2005 | Nemoto et al. | | 2005/0285547 A1 | 12/2005 | Piepgras |
| 2005/0024868 A1 | 2/2005 | Nagai et al. | | 2006/0002110 A1 | 1/2006 | Dowling et al. |
| 2005/0029688 A1 | 2/2005 | Hagmann et al. | | 2006/0007709 A1* | 1/2006 | Yuen .......................... 362/641 |
| 2005/0030744 A1 | 2/2005 | Ducharme | | 2006/0012987 A9 | 1/2006 | Ducharme |
| 2005/0035728 A1 | 2/2005 | Schanberger et al. | | 2006/0016960 A1 | 1/2006 | Morgan et al. |
| 2005/0036300 A1 | 2/2005 | Dowling et al. | | 2006/0176703 A1 | 8/2006 | Cayton et al. |
| 2005/0040774 A1 | 2/2005 | Mueller et al. | | 2006/0193611 A1 | 8/2006 | Ballesteros et al. |
| 2005/0041161 A1 | 2/2005 | Dowling et al. | | 2006/0231213 A1 | 10/2006 | Matsuda et al. |
| 2005/0041424 A1 | 2/2005 | Ducharme | | 2006/0237439 A1* | 10/2006 | Norwood et al. ........... 219/506 |
| 2005/0044617 A1 | 3/2005 | Mueller et al. | | | | |
| 2005/0047132 A1 | 3/2005 | Dowling et al. | | | FOREIGN PATENT DOCUMENTS | |
| 2005/0047134 A1 | 3/2005 | Mueller et al. | | | | |
| 2005/0053368 A1 | 3/2005 | Pesu et al. | EP | 0617667 A1 | 10/1994 | |
| 2005/0053528 A1 | 3/2005 | Rymer | EP | 0705281 A1 | 4/1996 | |
| 2005/0062440 A1 | 3/2005 | Lys et al. | EP | 0736248 A1 | 10/1996 | |
| 2005/0063194 A1 | 3/2005 | Lys et al. | EP | 0945062 B1 | 9/1999 | |
| 2005/0068777 A1 | 3/2005 | Popovic | EP | 0956868 B1 | 11/1999 | |
| 2005/0069304 A1 | 3/2005 | He et al. | EP | 1 033 139 | 9/2000 | |
| 2005/0069306 A1 | 3/2005 | He et al. | EP | 1 219 308 | 7/2002 | |
| 2005/0069307 A1 | 3/2005 | He et al. | EP | 1332765 A1 | 8/2003 | |
| 2005/0099824 A1 | 5/2005 | Dowling et al. | EP | 1422249 A1 | 5/2004 | |
| 2005/0105186 A1 | 5/2005 | Kaminsky et al. | ES | 1005422 | 11/1988 | |
| 2005/0105296 A1 | 5/2005 | French | ES | 1015255 | 6/1991 | |
| 2005/0105303 A1 | 5/2005 | Emde | GB | 2277267 A | 10/1994 | |
| 2005/0116667 A1 | 6/2005 | Mueller et al. | GB | 2369816 A | 6/2002 | |
| 2005/0117365 A1 | 6/2005 | Menke | JP | 54-21247 | 2/1979 | |
| 2005/0122065 A1 | 6/2005 | Young | JP | 62094169 | 4/1987 | |
| 2005/0122292 A1 | 6/2005 | Schmitz et al. | JP | 1295808 | 11/1989 | |
| 2005/0122721 A1 | 6/2005 | Hori | JP | 2078077 | 3/1990 | |
| 2005/0122722 A1 | 6/2005 | Menke | JP | 2138577 | 5/1990 | |
| 2005/0128743 A1 | 6/2005 | Chuey et al. | JP | 2242633 | 9/1990 | |
| 2005/0128751 A1 | 6/2005 | Roberge et al. | JP | 3240701 | 10/1991 | |
| 2005/0133617 A1 | 6/2005 | Hidalgo et al. | JP | 5003744 | 1/1993 | |
| 2005/0146893 A1 | 7/2005 | Ford et al. | JP | 6003627 | 1/1994 | |
| 2005/0147523 A1 | 7/2005 | Laudamiel-Pelleet et al. | JP | 06-36643 | 5/1994 | |
| 2005/0147539 A1 | 7/2005 | Laudamiel-Pellet et al. | JP | 6155489 | 6/1994 | |
| 2005/0151489 A1 | 7/2005 | Lys et al. | JP | 6205929 | 7/1994 | |
| 2005/0157499 A1 | 7/2005 | Kim | JP | 06-262057 | 9/1994 | |
| 2005/0167522 A1 | 8/2005 | Wheatley et al. | JP | 07-009744 | 2/1995 | |
| 2005/0168986 A1 | 8/2005 | Wegner | JP | 7230847 | 8/1995 | |
| 2005/0174473 A1 | 8/2005 | Morgan et al. | JP | 08-084551 | 4/1996 | |
| 2005/0174777 A1 | 8/2005 | Cooper et al. | JP | 08-241039 | 9/1996 | |
| 2005/0178345 A1 | 8/2005 | Crapser | JP | 8278413 | 10/1996 | |
| 2005/0180736 A1 | 8/2005 | Zobele | JP | 09-074971 | 3/1997 | |
| 2005/0185392 A1 | 8/2005 | Walter et al. | JP | 9107861 | 4/1997 | |
| 2005/0185395 A1 | 8/2005 | Pinter | JP | 308422 | 12/1997 | |
| 2005/0191481 A1 | 9/2005 | He et al. | JP | 10014467 | 1/1998 | |
| 2005/0194460 A1 | 9/2005 | Selander | JP | 10057464 | 3/1998 | |
| 2005/0195598 A1 | 9/2005 | Dancs et al. | JP | 2004057548 | 2/2004 | |
| 2005/0196159 A1 | 9/2005 | Zobele | JP | 2004275371 | 10/2004 | |
| 2005/0201107 A1 | 9/2005 | Seki | WO | WO 91/15249 | 10/1991 | |
| 2005/0201944 A1 | 9/2005 | Kvietok et al. | WO | WO 96/04021 | 2/1996 | |
| 2005/0205916 A1 | 9/2005 | Conway et al. | WO | WO 97/13539 | 4/1997 | |
| 2005/0211790 A1 | 9/2005 | Kvietok et al. | WO | WO 98/19526 | 5/1998 | |
| 2005/0212404 A1 | 9/2005 | Chen et al. | WO | WO 98/58692 | 12/1998 | |
| 2005/0213352 A1 | 9/2005 | Lys et al. | WO | WO 01/43785 A1 | 6/2001 | |
| 2005/0213353 A1 | 9/2005 | Lys et al. | WO | WO 01/79752 | 10/2001 | |
| 2005/0214158 A1 | 9/2005 | Kvietok et al. | WO | WO 02/09772 | 2/2002 | |
| 2005/0218243 A1 | 10/2005 | Zobele et al. | | | | |
| 2005/0218838 A1 | 10/2005 | Lys et al. | | | | |

| | | |
|---|---|---|
| WO | WO 03/095334 | 11/2003 |
| WO | WO 2003098971 A1 | 11/2003 |
| WO | WO 2004071935 A2 | 8/2004 |
| WO | WO 2005/030276 | 4/2005 |
| WO | WO 2005/092400 | 10/2005 |

OTHER PUBLICATIONS

European Search Report, Appl. No. EP 04709400.8, dated Oct. 4, 2006.

* cited by examiner

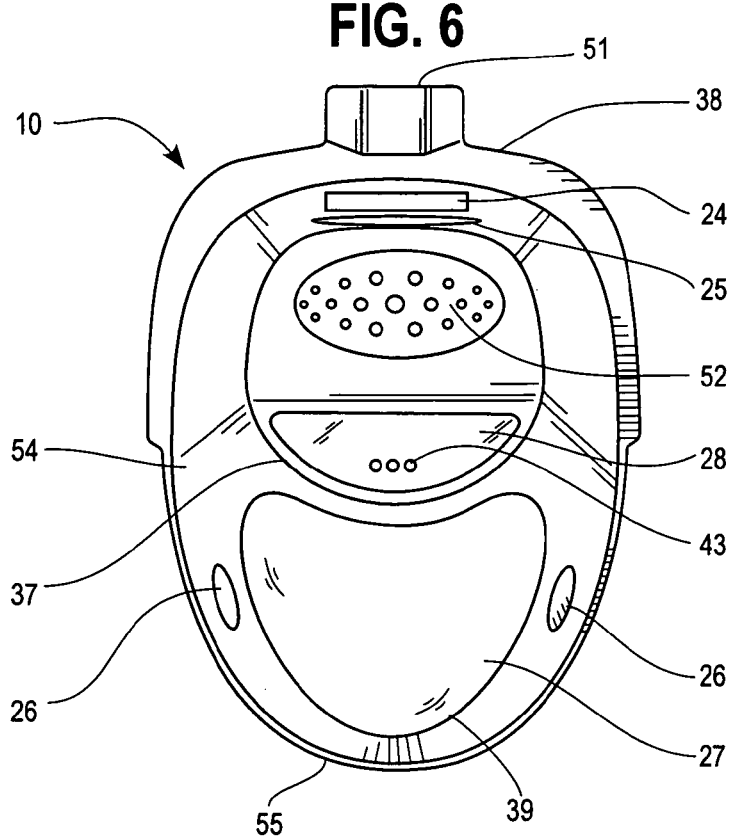
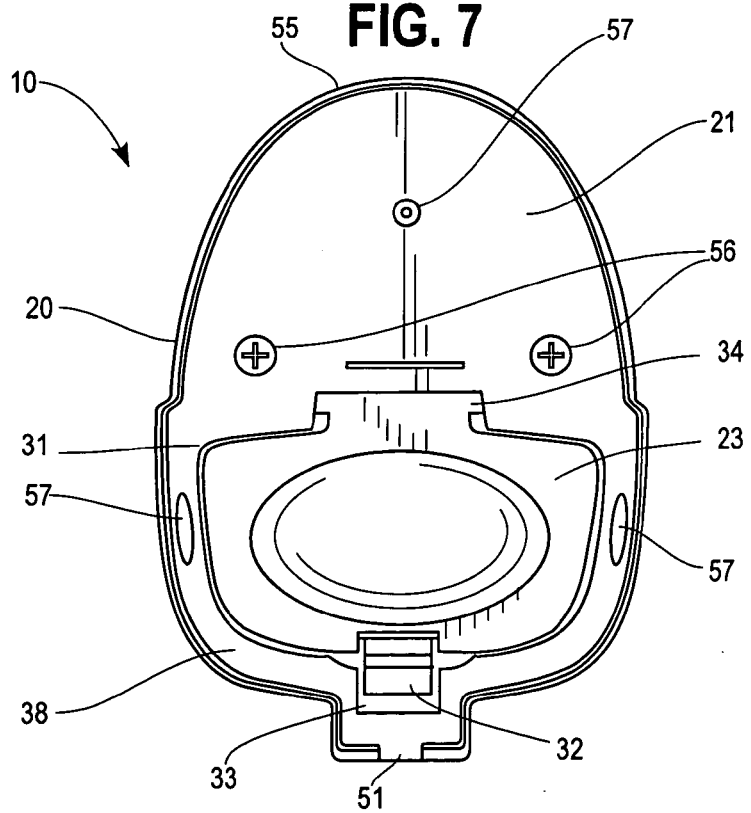

MULTI-CLARITY LENSES

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The invention generally relates to multi-clarity lens that diffuse and/or project a light source.

2. Description of the Background of the Invention

Lenses that diffuse light are known in the art. Devices that incorporate lenses are also known. One such device is a lighting unit for use with common household lighting fixtures that uses an illumination system near a wall or surface for creating an image of light thereon by passing radiant light through a convergent refracting lens. The lens in one instance is decorative in shape and embellished with etched, drawn, painted or applied designs for projecting the image.

Other devices that project light are nightlights that have a neon lamp or a number of light-emitting diodes (LED's) as the light source that are arranged in series with a current-limiting capacitor. In some cases, lighting devices emit different colors of light such as from multiple LED's.

Other devices that project light include a fragrance diffuser that is plugged directly into a wall socket and generates heat to facilitate diffusion of an active material, such as an air freshener or insect control material. Such diffusers are also known as heat-assisted evaporative dispensers.

One particular type of diffuser that plugs into a wall employs a liquid or gel air-treating composition in an enclosure having a permeable membrane, with all or part of the enclosure formed of a polymeric film. When heated, the air-treating composition migrates through the membrane and is released as a vapor at an outer surface. The use of this type of permeable polymeric membrane controls the dispensing of air-treating vapors and tends to eliminate great variations in rate of dispensing over the life of the product. Another conventional type of diffuser employs a liquid air freshener such as scented oil or a liquid insect repellant contained in a clear plastic container or bottle having a wick. One diffuser employs a ring-type heater mounted in the air freshener to vaporize and disperse the liquid contained in the container. Another device for evaporating a liquid from a container having a wick utilizes a sliding part coupled to a housing to displace and axially guide the container in a non-rotating manner in relation to a heating element to regulate an evaporation rate of the liquid. One vapor dispensing unit uses a variable temperature heater configured as a positive temperature coefficient (PTC) heater to control the evaporation level of fragrance. Yet another vaporizing device uses a guidance system between a refill bottle having a wick and a housing unit to aid in guiding a refill bottle unit relative to the housing unit and to center the wick contained in the refill bottle unit relative to a heating element contained within the housing unit when the refill bottle is inserted into the housing unit.

In some instances, a liquid evaporator uses a refill bottle that has an engagement portion that engages a casing of the liquid evaporator and a release that causes deformation of the receiver and to allow release of the container from the casing.

Various types of fragrance dispensers other than the evaporative type use an electrostatic vapor or an aerosol generator for supplying aromatic oil, deodorant, disinfectant, fumigant, fungicide, insecticide or bactericide, to a room. In some cases, an adjustable aerosol dispenser is provided for supplying different amounts of fragrance into a room according to sensed light, odor, sound, etc. In other cases, a device is provided for emitting a vaporized substance into the atmosphere according to the setting of a timer. In yet other cases, an electrostatic sprayer that sprays insecticides is controlled according to selected "on" times and "off" times and also incorporates a sensor to sense the available power for continued operation. Other dispensers have an ultrasonic liquid atomizer with automatic frequency control, or have timers for controlling the operation of the dispensers according to preset times.

Additional dispensers of a type often referred to as diffusers have a fragrance warmer that incorporates a plug-through capability and an incandescent nightlight. Incandescent nightlights, however, suffer from various disadvantages. For example, incandescent bulbs produce considerable heat. When incandescent nightlights are used in connection with a diffuser of volatile active material, the heat generated by the incandescent nightlight tends to affect the rate at which the active material is diffused. Thus, when the nightlight is turned on, the active material may, for example, diffuse too quickly. Also, because of the added heat, it is difficult to regulate the rate at which the active material is diffused. Another disadvantage of using incandescent bulbs as nightlights is that the bulbs tend to consume relatively large amounts of energy. Since nightlights are often left on for extended periods of time in multiple rooms of a house, this energy consumption may be a significant consideration.

Various techniques, such as using different incandescent bulbs and using bulbs of varying size or power rating, have been used in an attempt to reduce heat produced and power consumed by nightlights. These techniques, however, have yielded only minor reductions in heat emission and energy consumption, and come at a cost to performance of the nightlight.

Another problem with conventional diffusers is that the diffusers do not make effective use of lighting elements. For example, lighting elements in conventional diffusers are typically not used to generate aesthetic lighting displays, such as multicolored displays, color-changing displays, projection displays, shine-through displays, or the like. A still further problem is that conventional diffusers are limited in use to locations where wall sockets are already exist. Wall sockets are often located in places that are less than ideal for placement of diffusers, such as near the floor, in a corner, etc. This limitation on the location of diffusers is even more problematic for diffusers that have a lighting element or display, since the diffuser often cannot be located in a user's line of sight, thereby limiting the effectiveness of the lighting element. Yet another problem is that conventional diffusers typically do not have suitable controllability for varying the emission of light and/or fragrance. In particular, such diffusers seldom have fragrance dispensers that are easily and precisely adjustable to vary a fragrance intensity or diffusion rate.

SUMMARY OF THE DISCLOSURE

The present invention is directed toward apparatuses, devices, methods, kits, programs, and combinations to disperse and/or project light. Illustratively, in one embodiment of the present invention a diffuser that disperses an active material is provided that has a housing assembly having a compartment for receiving a container that may be configured to include an optional wick extending therefrom to assist in, for example, the evaporation and/or dispersion of the active material; an optional heating device disposed within the housing assembly at a position proximate to the container and/or an upper portion of the wick if present; an electrical connection to transmit electricity to the diffuser; at least one light source comprising a light-emitting diode; and at least one lens to project light emitted from the light source from the diffuser.

In some embodiments of the present invention, the diffuser has two or more lenses with at least one of the lenses oriented toward at least one of a front, side, top, bottom, or back side of the diffuser: The lens or lenses may be made of any suitable material that transmits light including glass, resin, and/or plastic, and combinations thereof. An illustrative plastic useful in the present invention is polypropylene. The lens or lenses may also be configured to diffuse light and project light from the diffuser. The lens or lenses of the present invention may also be constructed as a single piece of material such as an integral optical element or multiple pieces such as multiple optical elements. A lens of the present invention may also have at least one section or portion that is thicker than at least one other section of the lens. In some embodiments, the thicker section or portion of the lens is more opaque to light than a thinner section of the lens. One or more sections or portions of a lens of a present invention may also be clear, polished, frosted, colored, etched, painted, and/or textured.

In other embodiments a diffuser of the present invention also includes an adjustment mechanism for displacing the container and/or an upper portion of a wick if present toward or away from a heating device disposed in the diffuser.

A method of displaying light and dispensing a fragrance and/or an active material from a diffuser is also provided by the present invention. The method includes providing a diffuser that has a housing assembly with a reclosable compartment for at least one of receiving, releasably engaging, and/or retaining a container configured to contain the fragrance and an optional wick extending therefrom; an optional heating device disposed within the housing assembly at a position proximate to the container; a light source; and at least one lens near the light source to display light; inserting into the compartment the container having an amount of the fragrance; providing a power source to the diffuser; and activating the light source to display the light through at least one of the lenses, and the optional heater if present to assist in dispensing the fragrance and/or the active material from the diffuser. In some embodiments, the diffuser has at least two lenses, and/or at least one lens diffuses light and projects light.

In yet other embodiments of the present invention, a multi-clarity lens for displaying light from a device, which, for example, also disperses an active material, is provided. The multi-clarity lens may be any suitable transparent or semitransparent material including, for example, polypropylene. The lens may also have at least one section that is thicker and more opaque to light than at least one other section. A device useful in the present invention includes a device that has a housing assembly with a compartment for at least one of receiving, releasably engaging, and/or retaining a container configured to contain the active material and an optional wick extending therefrom; an optional heating device disposed within the housing assembly at a position proximate to the container; a light source, including for example, a light-emitting diode; and at least one polypropylene lens near the light source to display light. In one embodiment, the multi-clarity lens of the present invention diffuses light and projects light. The multi-clarity lens of the present invention may also include one or more sections or portions that are clear, polished, frosted, colored, etched, painted, and/or textured.

Other aspects and advantages of the present invention will become apparent upon consideration of the following detailed description.

BRIEF DESCRIPTION OF THE DRAWINGS

FIG. 6 is a plan view of the embodiment of FIG. 1;

FIG. 7 is a bottom elevational view of an embodiment of FIG. 1 with a reclosable door in a closed position;

FIG. 18A is a cross-sectional view taken generally along the lines 18A-18A of FIG. 18 depicting a lens.

DETAILED DESCRIPTION OF THE DISCLOSURE

Figure 1:
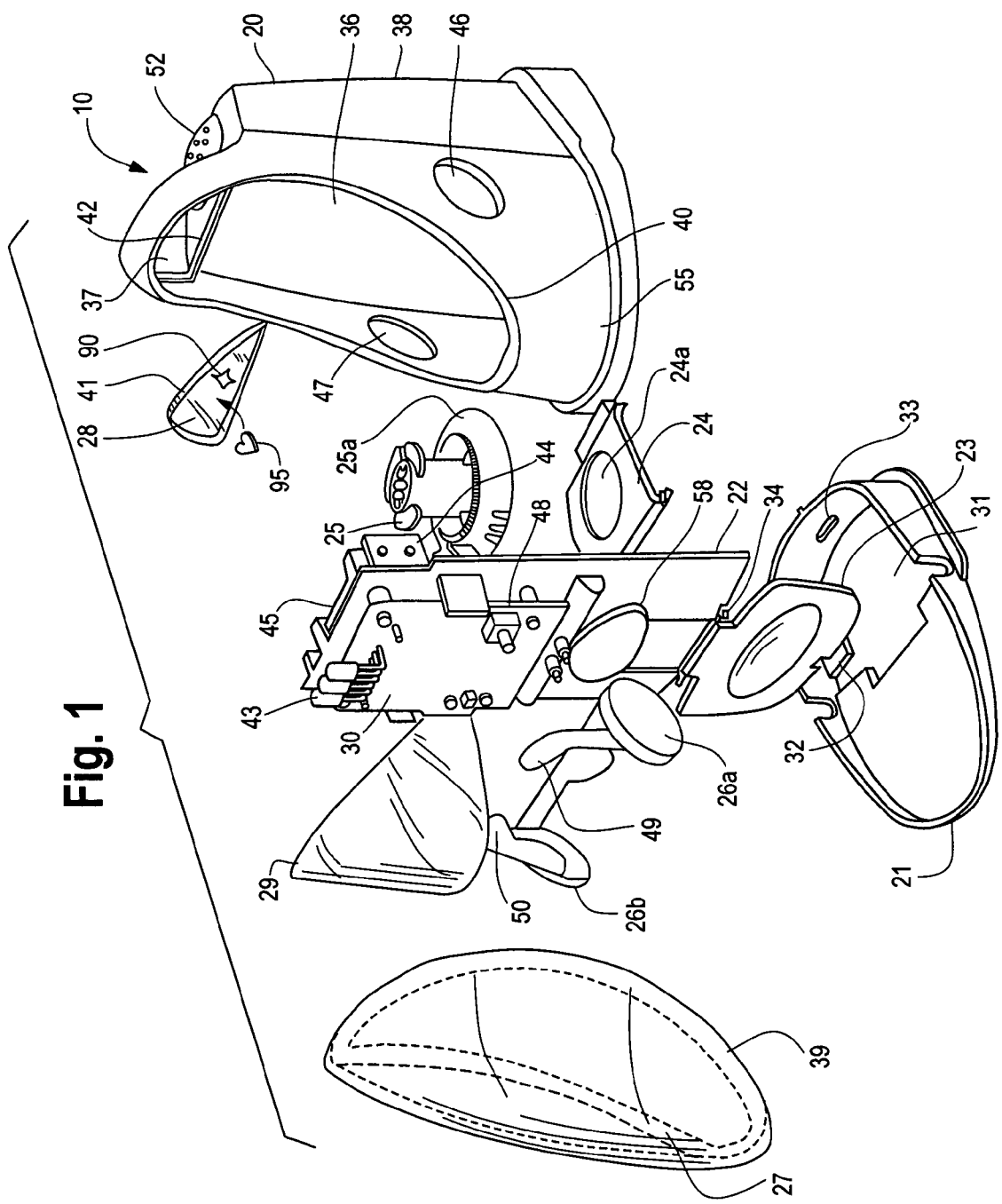
FIG. 1 is an exploded isometric view of a diffuser of the present invention, showing the internal electronic and mechanical components of the diffuser.

The present invention is directed toward apparatuses, devices, methods, kits, programs, and combinations to disperse and/or project light. While the present invention may be embodied in many different forms, several specific embodiments are discussed herein with the understanding that the present disclosure is to be considered only as an exemplification of the invention and is not intended to limit the invention to the embodiments illustrated. For example, in one embodiment of the present invention where a light effect of glowing, diffused, and projected light is desired, one lens is provided that has a section or portion that diffuses light in one section of the lens and is substantially clear in another section to allow substantially all the light to pass through the lens. In other embodiments to obtain the same effect, one or more lenses diffuse light while one or more other lenses are clear to allow substantially all the light to pass through the lens(es).

A lens of the present invention may be an integral optical element or multiple optical elements depending on, for example, the light effect desired, the materials used to make the lens(es), and/or the manufacturing technique used. Illustratively, a lens of the present invention that disperses and projects light comprises a single optical element and has sections or portions of various thicknesses, including a thin section that is substantially clear and/or transparent and another section of a thickness with increased opaqueness. In one embodiment of the present invention, as the thickness of the lens increases the opaqueness increases in proportion to the increase in thickness and provides for more light diffusion. In other embodiments, however, as the thickness of the lens increases little or no change in opaqueness occurs and other methods to increase opaqueness including, for example, frosting, etching, and/or blocking portions of the lens are utilized to disperse the light. In order to reduce cost and manufacturing steps, a one-piece or multiple-piece lens of an inexpensive material, for example, polypropylene, may be used. Standard molding process known to those skilled in the art may also be used in the present invention to form a desired lens or lenses of various shapes, thicknesses, and/or configurations.

The lens(es) of the present invention may be used in any application where diffused or dispersed and non-dispersed, non-diffused or projected light is desired. For example, a device useful in the present invention includes a diffuser that has a light source and dispenses an active material such as, for example, a fragrance and/or an insecticide, to the atmosphere through, for example, evaporation, heat, and/or air movement. In other embodiments, the light source is ambient or passive. For example, packaging materials may include a lens of the present invention where a portion of the inside of the package is desired to be blocked and/or obscured, while other areas are desired to be clear and/or translucent to allow a viewer to view the inside of the package. Examples of packaging materials useful in the present invention include computer and/or electronic cases such as, for example, a laptop computer, a desktop computer, a telephone, a music player, a stereo system, a television, a watch, a video game, and/or a media device that plays, for example, music, movies and/or games, and may or may not include an internal light source. Display cases also are useful in the present invention and also may or may not include a light source that is projected through one or more lenses. Such display cases may include one or more areas of the lens that magnify the contents of the display case. Another device useful in the present invention is a lighting fixture with at least one light source, for example, a light bulb such as, for example, an incandescent bulb, a fluorescent bulb, and/or a halogen bulb, a LED, and/or a candle, in which one or more lenses of the present invention are incorporated into the lighting fixture to project light and/or shadows from the lighting fixture. Such lighting fixtures may be, for example, decorative for use in a home or office setting, for example, or a safety lighting fixture such as emergency lighting fixtures and/or lighting fixtures for lighting stairs or stairwells. Other devices useful in the present invention may also include other sensory devices such as light, sound, motion, smoke, fire, and/or carbon monoxide sensors that in one embodiment incorporate a light source that may be used in coordination with another sensory device. The lens(es) utilized with the devices described herein may be configured to project any desired image onto a projection surface such as a smooth surface, a wall, a floor and/or a ceiling. For example, one or more lenses incorporated into a motion detector may be configured to project an image of a dog and/or a security guard onto a wall when the motion detector is activated. In other embodiments, a lens of the present invention is useful in medical devices and/or research tools, including, for example, devices that incorporate visual light, for example, a microscope, ultraviolet light, luminescent light, and/or x-rays, and combinations thereof, including, for example, a synchrotron light source of various energy ranges. Other light sources useful in the present invention include lasers that emit monochromatic radiation, such as, for example, nitrogen and/or dye lasers, which may be high- or low-energy and/or pulsed. A light projection device of the present invention can also be used in the home and/or office to create light patterns for relaxation or amusement. For example, a night light for children may be used with stickers and/or patterns on clear film that can be placed over the lens to project a child's name, initials, sport team logo, animal, and/or favorite object. In other embodiments, a night light with light projection can direct people in an unfamiliar environment (such as a hotel/motel) to the nearest exit.

The present invention is further illustrated by the following drawings, which should not be construed as limiting in any way. For example, while the following drawings are illustrated with particular reference to one or more LED's, it is understood that any other light source of any energy range and/or wavelength may, if desired, be substituted in whole in part for the LED's herein described. Additionally, while the following drawing are illustrated with particular reference to a diffuser, it is understood that any other device utilizing a light source may, if desired, be substituted in whole or in part for the diffuser herein described.

As shown in FIGS. 1-10, a diffuser 10 of the present invention includes a housing assembly 20 with a base 21 having an opening 31 to receive a refill bottle 100. The housing assembly 20 of the diffuser 10 may be made of any suitable material including, for example, a plastic such as polypropylene and/or high-density polyethylene. Referring to FIG. 1, the housing assembly 20 includes a chassis 22 to support various components of the diffuser 10 and is shown with a bottom door 23 in an opened position. The bottom door 23 is attached to the chassis 22 via a living hinge 34. When the door 23 is in a closed position (see FIG. 7) a latch 32 engages the base 21 to secure the door in a closed position. The chassis 22 holds a printed circuit board 30 that controls the function of one or more components of the diffuser 10. A light source 43 includes three light-emitting diodes (LED's) that are disposed on the printed circuit board 30 and are configured to project light through a front lens 27, a diffuser lens 29, and a back lens 28. While this embodiment illustrates a light source 43 with LED's, a device of the present invention may use a single LED, a plurality of LED's, and/or one or more LED arrays. If multiple LED's are used, they may be arranged in, for example, a line, a circle, a square, a triangle, a flower shape, an arc shape, or any other desired shape or arrangement.

The front lens 27 is configured to be disposed in an opening 36 at a front side 55 of the housing assembly 20 and to attach to the housing assembly along an outer edge 39 of the front lens and an edge of the front opening 36. The back lens 28 is configured to be disposed in an opening 37 at a back side 38 of the housing assembly 20 and to attach to the housing assembly along an outer edge 41 of the back lens and an edge of the back opening 42. A diffuser lens 29 is disposed between the front lens 27 and the light source 43 and is attached to the chassis 22 at a pair of contact points 44 (only one shown). In other embodiments, a one-piece lens of various thicknesses replaces the two lens configuration of the front lens 27 and the diffuser lens 29 as shown in FIG. 1. In this embodiment, the front lens 27 and back lens 28 are shaped so as to snap-fit tightly onto the housing assembly 20, and in other embodiments may also be securely fastened to the housing assembly by use of, for example, an adhesive, a tab, and/or a clip. A plurality of top vents 52a are disposed on the housing assembly 20 above an interior compartment 59 (see FIGS. 8 and 9) that houses the refill bottle. In this embodiment, a fan-like recess 58 disposed in the chassis 22 and positioned below an ejector arm 24 is configured to engage the refill bottle and to assist in receiving, releasably engaging, and/or retaining the refill bottle in the diffuser 10.

A heater 45 is also attached to the chassis 22 and in this embodiment is a resistance heater located in proximity to the interior compartment 59 of the housing assembly 20 of the diffuser 10 to heat an active material (not shown) received in the interior compartment. A heating element useful in the present invention may be of any desired shape and/or may be complementary with the shape of a wick or wicks utilized in the present invention and/or a housing assembly 20 of a device. Illustratively, the heater 45 is a metal oxide 6 kΩ resistor potted in a ceramic block, which is capable of handling up to at least about 5 W. Other heaters useful in the present invention include, for example, a wire-wound heater, a printed ink circuit, an etched foil heating device, a positive temperature coefficient heater (PTC), or the like. An example of a resistor heater is available from Great Land Enterprise Co., Ltd., of Shenzhen, China. Variable temperature heaters may also be used in the present invention, including, for example, the heating devices disclosed in U.S. Pat. No. 6,661,967, by Levine, et al. Other heaters useful in the present invention are disclosed in, for example, U.S. Patent Publication No. 2004/0035409, by Harwig, et al. Combinations of the above heating elements may also be used in the present invention. A diffuser 10 of the present invention may also include multiple heating elements depending on, for example, the number of wicks utilized in the diffuser. As should be evident to one of ordinary skill in the art, the heater 45 may be continuously energized, or may be provided an alternating waveform, such as a pulse-width modulated waveform having a duty cycle selected to cause the heater 45 to develop a desired heat level.

In other embodiments, a pumping device to facilitate the diffusion of an active material by pumping out a portion of an active material fluid is used instead of or in conjunction with a heating element. A pumping device useful in the present invention includes, for example, a piezoelectric atomizing pump. In one embodiment of the present invention, a piezoelectric frequency generator, for example, a piezoelectrically actuated atomization device, controls the operation of a fragrance dispenser. The atomization device typically operates to atomize fragrance for an approximately eleven millisecond burst at set intervals. The piezoelectric frequency generator controls the frequency of the eleven millisecond bursts to adjust the rate at which the fragrance is dispensed (thus, controlling the potency of the aroma). Typically, the piezoelectric frequency generator operates using pulse width modulation. A piezoelectric atomizing pump useful in the present invention is disclosed in, for example, U.S. Pat. No. 6,450,419. Another example of a piezoelectric atomizing pump useful in the present invention is disclosed in, for example, U.S. Pat. No. 6,292,196. Yet another example of a piezoelectric atomizing pump useful in the present invention is disclosed in, for example, U.S. Pat. No. 6,341,732.

Figure 4:
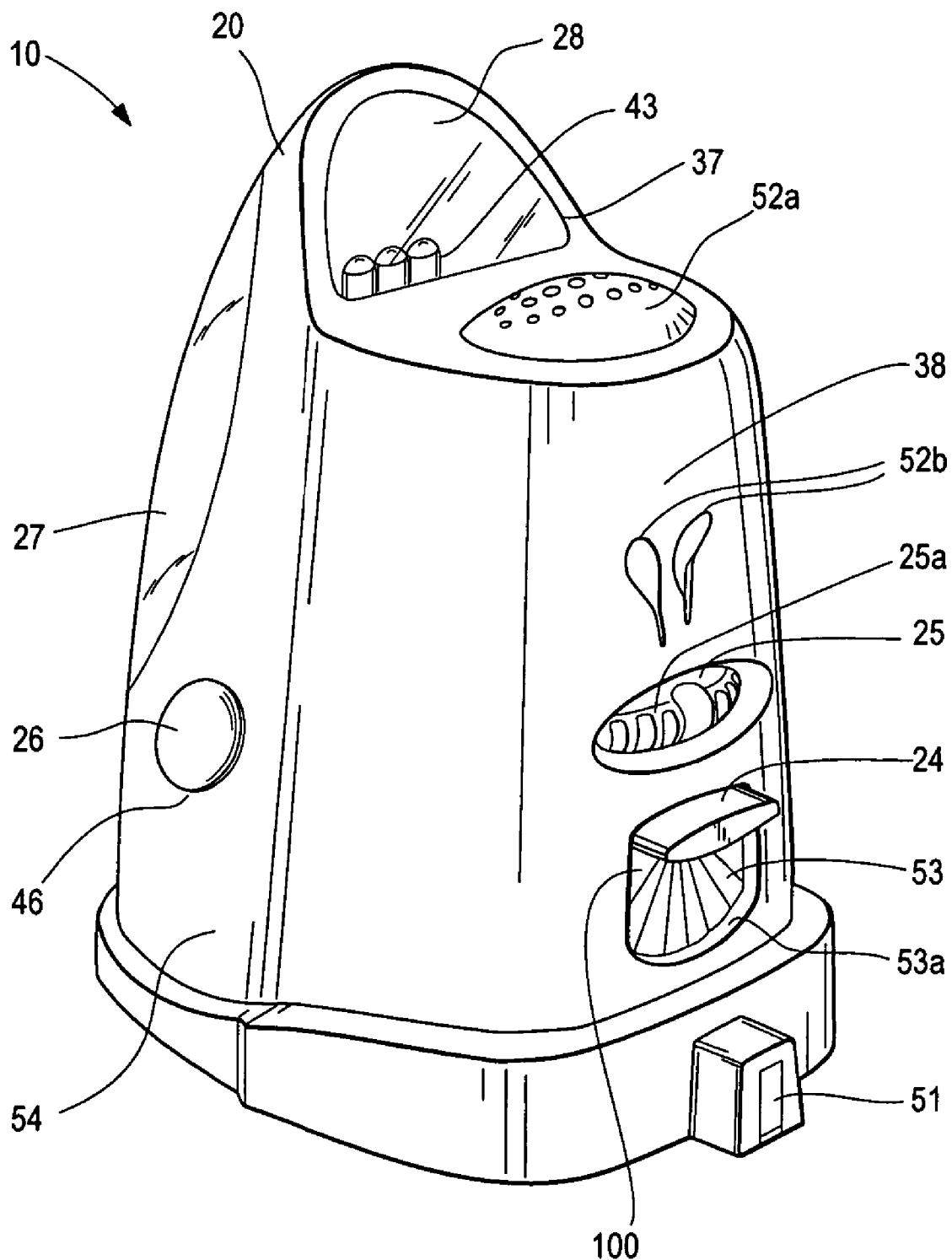
FIG. 4 is an isometric view of an embodiment of FIG. 1.

As shown in FIG. 4, a wick adjustment mechanism 25 is disposed in the housing assembly 20 above the ejector arm 24 for displacing an upper portion of a wick 101 (see FIG. 9) toward or away from the heating element 45. The adjustment mechanism 25 varies the rate at which the active material is diffused by moving the wick 101 of the container 100 toward the heating element 45 to increase the diffusion rate and away from the heating element to decrease the diffusion rate by movement of a dial 25a. Other wick adjustment mechanisms useful in the present invention include those described in, for example, U.S. Patent Application Publication No. 2003/0138241 A1.

Two user interactive buttons 26a, 26b are disposed in two openings 46, 47, respectively, in the housing assembly 20 of the diffuser 10, and are configured to operatively interact with the printed circuit board 30 via two switches 48a, 48b on one or both sides (the second switch is not shown in FIGS. 1-10, but is shown schematically in FIG. 11) of the printed circuit board 30. Illustratively, a user pushes the interactive buttons 26a, 26b to displace a respective button assembly arm 49 or 50 into engagement with the respective switches 48a, 48b to control operation of the LED's 43.

Other configurations of LED's may also be used in a diffuser 10 depending on the particular light effect that is desired, including, for example, a nightlight, a multicolored display, a color-changing display, a projection display, and/or a shine-through display. For example, a diffuser 10 may include one or more LED's and/or one or more LED arrays of one or more colors and/or luminosities. One or more of LED's may also be used as a low-temperature, low-power light such as, for example, a nightlight, and/or an ornamental display. Illustratively, the LED has a luminous intensity rating at 20 milliamps (mA) preferably of between about 50 millicandela (mcd) to about 10,000 mcd, or more preferably between 100 mcd to about 5,000 mcd, or more preferably less than about 1,300 mcd, or more preferably less than about 5,000 mcd. Where multiple LED's are utilized, each of the LED's has a luminous intensity rating of less than the above luminous intensity ratings, but on total have a luminous intensity rating of as described above. The one or more LED's may also be provided in combination and/or in coordination with other sensory stimulation, such as fragrance and/or sound. For example, a red and/or green LED could be used with an appropriate fragrance and/or sound during the holidays. Where multiple LED's and/or one or more LED arrays are utilized in the present invention, each LED or LED array may be controlled independently or together, to provide a desired ornamental design or effect. An example of a diffuser with coordinated emission of fragrance, light, and/or sound useful in the present invention is disclosed in, for example, PCT Patent Application No. PCT/US04/003533. Another example of a diffuser with coordinated emission of fragrance, light, and/or sound useful in the present invention is disclosed in, for example, PCT Patent Application No. PCT/US03/12469. Music or acoustic generators useful in the present invention for generating sound and/or playing sounds/music stored in a memory is disclosed in, for example, U.S. Pat. No. 5,483,689. Other music or acoustic generators useful in the present invention for generating sound and/or playing sounds/music stored in a memory is disclosed in, for example, U.S. Pat. No. 5,452,270. Yet other music or acoustic generators useful in the present invention for generating sound and/or playing sounds/music stored in a memory is disclosed in, for example, U.S. Pat. No. 6,423,892. A diffuser 10 of the present invention may also include speakers for emitting music, sounds, and the like, and to produce a suitable effect in connection with a light presentation and/or an aroma or a fragrance released from the diffuser. A programmable user control, including, for example, a remote control, may also be provided to program the operation of one or more LED's, speakers, and/or fragrance dispensers. The user control may include an on/off switch which activates and/or deactivates, for example, the LED's, speakers, and/or fragrance dispensers.

A light presentation may also be activated automatically in response to a signal from a sensor, including, for example, an ambient light sensor device 220 that detects light, a temperature detector, a sound detector, a smoke detector, a carbon dioxide detector, a fire detector, a fragrance detector, and/or a motion detector. For example, a light sensor may be set such that when a predetermined amount of light is detected (indicating, for instance, sunset or sunrise, a room light being turned on or off, or the like), the sensor activates one or more preprogrammed presentations stored in memory of a device of the present invention. One such ambient light sensor device useful in the present invention is disclosed in, for example, U.S. Pat. No. 6,478,440. Additionally, a user may program a device of the present invention to produce a personalized presentation. For example, one or more buttons may be configured to allow a user to program the fragrance aspect of the presentation. Illustratively, once a button has been pressed, the user may press another button to determine the starting rate of fragrance emission. The starting rate may also be set by pressing a button to reduce the fragrance emission rate and/or pressing another button to increase the rate. The selected rate may also be displayed on a display. Once the starting rate is set, the user may also press a button to choose an ending rate for the fragrance emission in a manner similar to that for setting the starting rate. Once set, the dispenser alters the rate of emission of fragrance over the course of the presentation from the set starting rate to the set ending rate.

Figure 2:
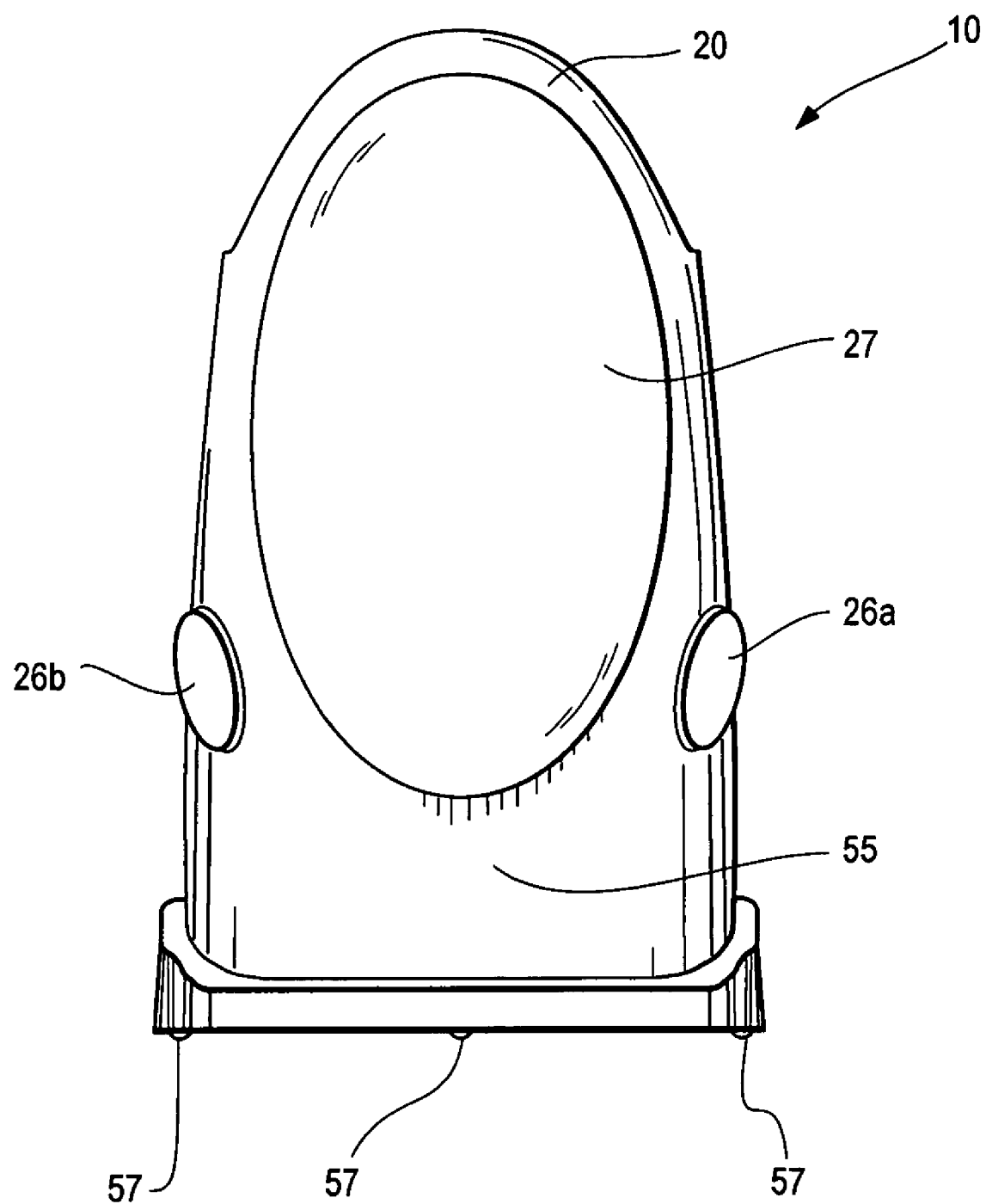
FIG. 2 is a front elevational view of an embodiment of FIG. 1.
Figure 3:
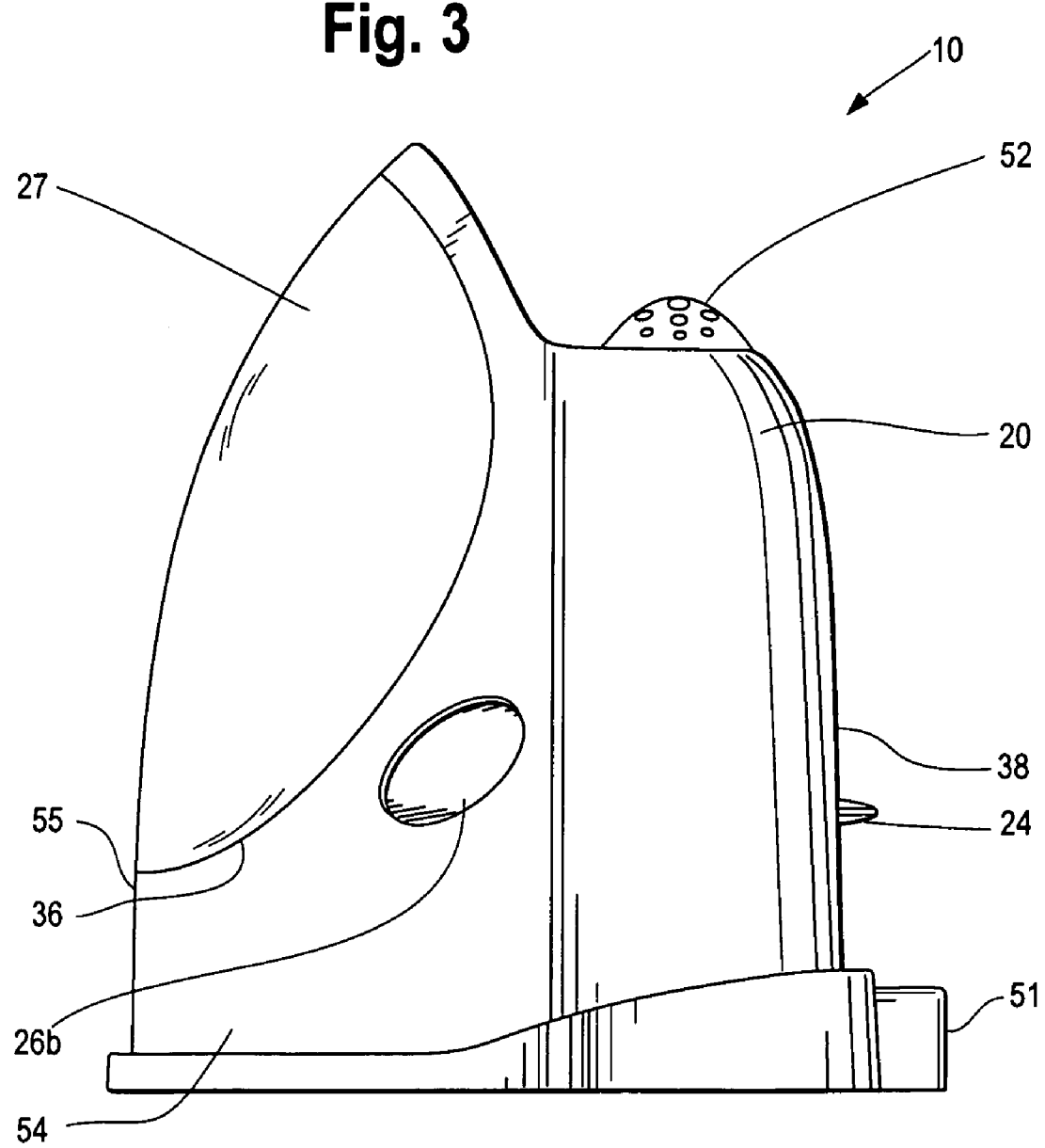
FIG. 3 is a side elevational view of an embodiment of FIG. 1.

FIG. 2 illustrates an exterior frontal view of the diffuser 10. The front side 55 of the housing assembly 20 is shown. Feet or pads 57 are provided to stabilize the diffuser 10 when placed on a surface. An exterior side view of the diffuser 10 is provided in FIG. 3. On a side 54 of the diffuser 10 the button assembly 26 may be seen. A plurality of top vents 52a are disposed on the housing assembly 20 above an interior compartment 59 (see FIGS. 8 and 9) that houses the refill bottle or container 100 (see FIG. 9). In other embodiments, the diffuser 10 may also have at least one top vent 52a disposed in the housing assembly 20 above the upper portion of a wick 101 that is inserted into the diffuser and an inlet opening 52b disposed in the housing assembly below the upper portion of a wick and each having a total opening area of about 0.25 to about 5 times the area of the cross-sectional area of the top of the wick. In some instances where condensation may form within the interior compartment 59, the total area of top vent 52a and the inlet opening 52b is between about 1 to about 3 times the area of the cross-sectional area of the top of the wick 101, depending on the manner in which the wick adjustment mechanism 25 moves the wick in relation to the opening. One consideration in the size of the top vents 52a and the inlet openings 52b is to reduce or eliminate condensation from the interior compartment 59, by configuring the top vents and inlet openings such that a vapor plume from evaporation of the active material is not blocked by the interior compartment 59 or housing 20. However, if the top vents 52a and inlet openings 52b are too large, there is too much air flow into the interior compartment 59, which cools the top of the wick 101 slowing active material weight loss efficacy.

In one embodiment of the present invention the top vents 52a and inlet openings 52b are no wider than about 0.25 inch (0.64 cm) such that a rod having a diameter of about 0.25 inch (0.64 cm) cannot be inserted through the top vents and inlet openings. In this embodiment the top vents and inlet openings may be shaped such that a top vent or inlet opening has no cross section greater than about 0.25 inch (0.64 cm). Such shapes include, for example, tear-drop shapes, oblong shapes, oval shapes, square shapes, triangle shapes, and the like. Illustratively, the top vents and inlet openings 52a, 52b may provide a "chimney effect" inside the interior compartment that houses the refill bottle or container so that airflow or air movement occurs across the refill bottle or container to assist in vaporizing the active material and dispersing the vaporized active material from the diffuser 10. The top vents and inlet openings 52a, 52b may be formed in the housing 20 during the molding thereof and/or during a post-manufacturing process. The top vents and inlet openings 52a, 52b may also be decorative as well as functional and be used, for example, to project a light pattern from the diffuser 10.

Figure 5:
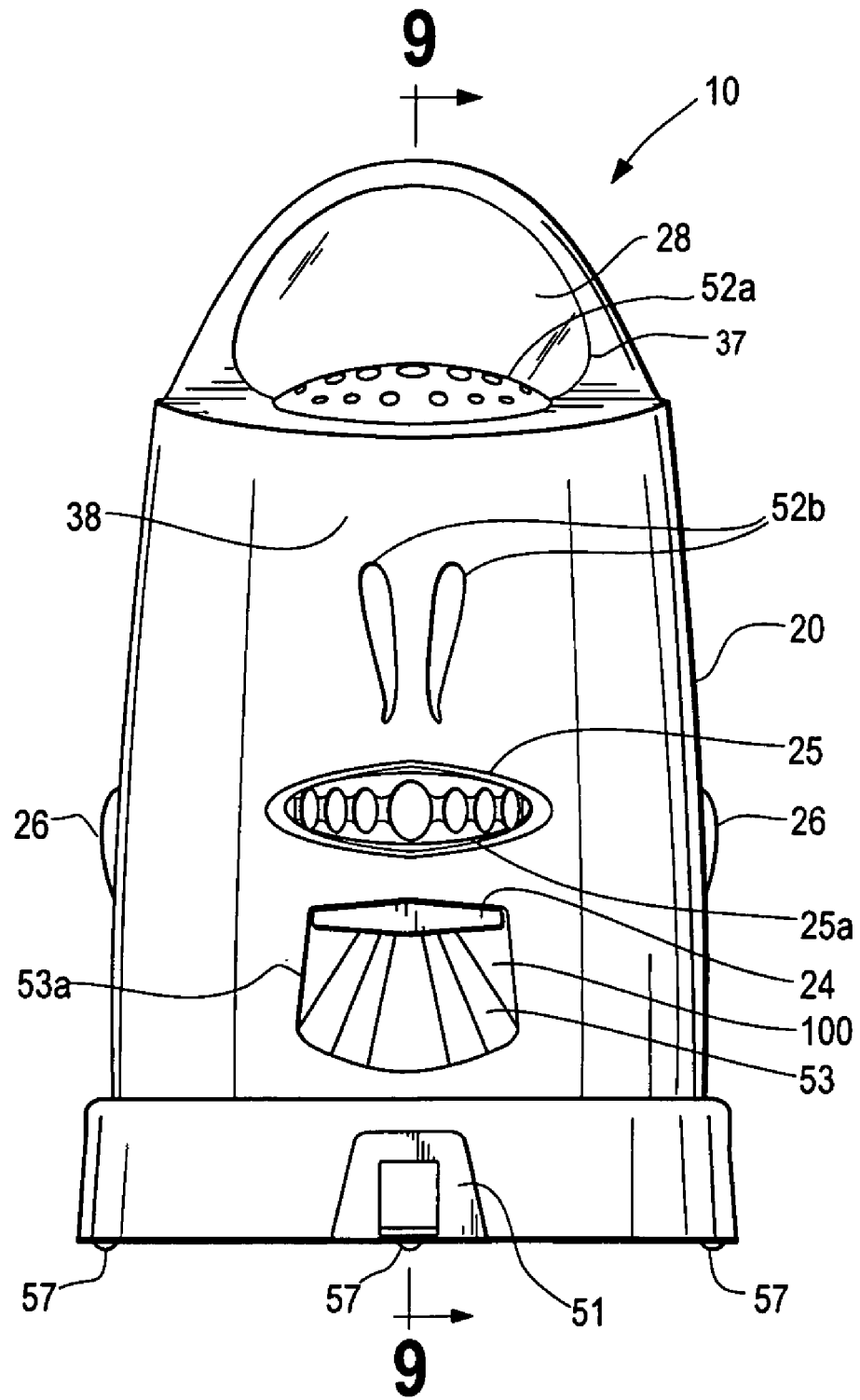
FIG. 5 is a back elevational view of an embodiment of FIG. 1.

An exterior back view of the diffuser 10 is provided in FIGS. 4 and 5. The back lens 28 is shown disposed in the opening 37 of the housing assembly 20. The wick adjustment mechanism 25 is disposed in the back side 38 of the housing assembly 20 above the ejector arm 24. An opening 53a in the back housing 38 is configured to engage a fan-like protrusion 53 of an inserted refill bottle 100 (See FIG. 9) below the ejector arm 24 and is configured to engage a refill bottle and to assist in receiving, releasably engaging, and/or retaining a refill bottle in the diffuser 10. A plurality of top vents 52a are disposed on the housing assembly 20 above an interior compartment 59 (see FIGS. 8 and 9) that houses the refill bottle 100, and a plurality of vent openings 52b are disposed on the back housing 38 to assist in movement of air into the interior compartment.

An outlet 51 in the housing assembly 20 is provided for an electrical wire or cord (not shown) to transmit electricity, for example, from a wall socket, to the diffuser 10 and to provide power to one or more components of the diffuser 10. The diffuser 10 may also include an electrical receptacle (not shown) that is electrically connected to one or more the components of the diffuser for receiving a plug of the electrical cord that supplies electrical power to the diffuser, or may be plugged directly into an electrical power source, such as, for example, an electrical wall outlet or socket. Illustratively, the diffuser 10 is configured to be a direct-corded diffuser with a plug at the end of the electrical cord that may be plugged into an electrical power source such as an electrical wall outlet or socket. A cord or wire may also be disposed in either the upper or lower portion of a housing assembly 20 of a diffuser 10, and/or may be configured as a separate element that is interposed between the upper and lower portions of the housing assembly during assembly. The plug may also be secured to the housing assembly 20 in a manner that allows the plug to rotate relative to the housing assembly in order to support the diffuser 10 in an upright position in both horizontal and vertical wall outlets.

A top view of the diffuser 10 is provided in FIG. 6. The light source 43 includes three LED's that are positioned in-line to project light through the front lens 27 and the back lens 28.

Figure 8:
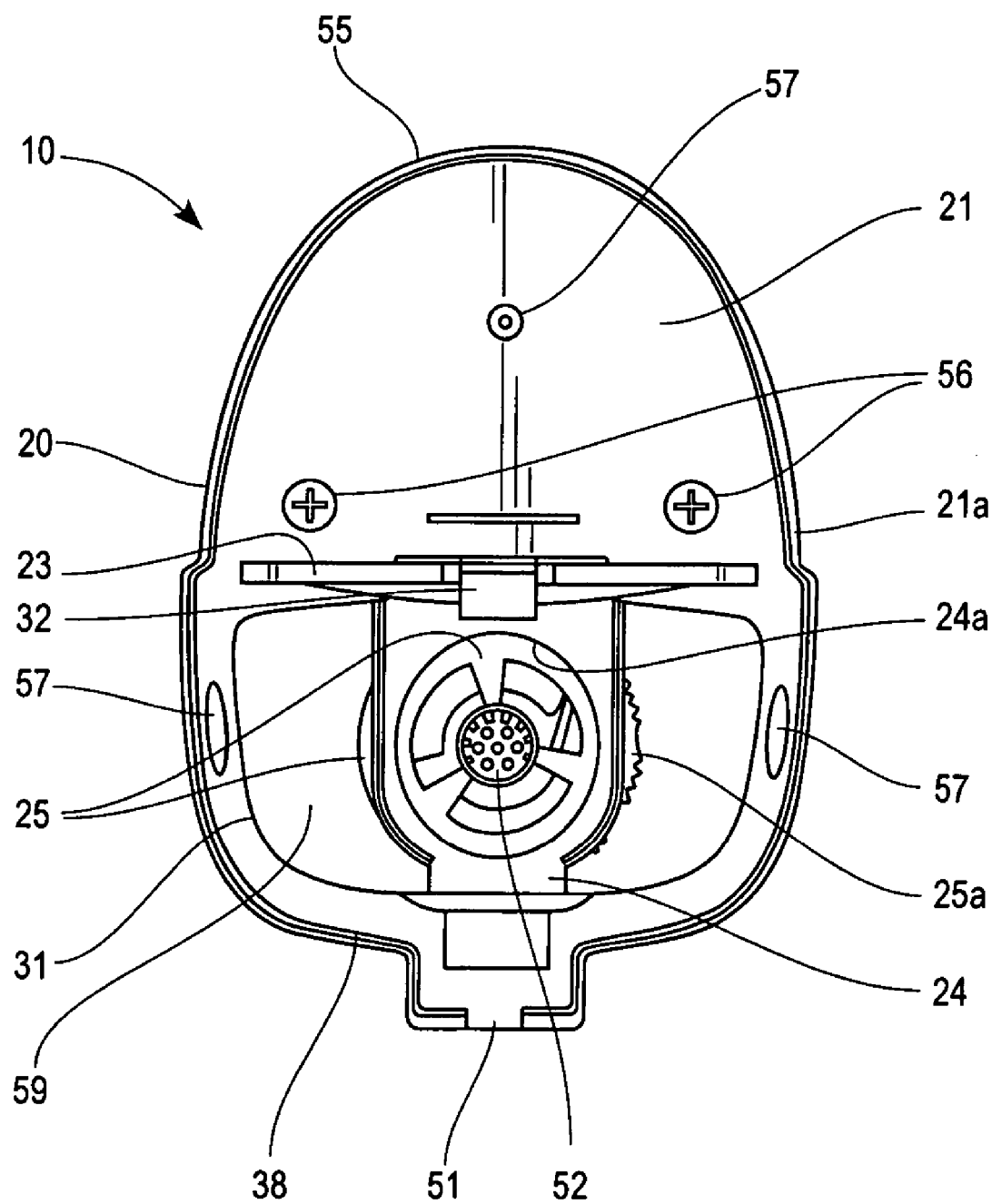
FIG. 8 is a bottom elevational view of an embodiment of FIG. 1 with a reclosable door in an open position.

A bottom view of the diffuser 10 is illustrated in FIGS. 7 and 8. The base 21 with the opening 31 is shown disposed inside the housing assembly 20. Two cross-notch-head screws 56 secure the base 21 to the housing assembly 20. In other embodiments, the screws are designed to be non-removable with common household tools like screwdrivers and pliers. In other embodiments rivets, welding, heat staking, adhesive bonding, special screws, and/or other fasteners, and combinations thereof, not readily removable by most common household tools are used to join and/or secure various components of the devices together. In yet other embodiments, various components are joined and/or secured together by fasteners that are easily removed by common household tools, including, for example, cross-notch-head screws, spring clips, and/or bent tabs, and combinations thereof.

As shown in FIG. 7, the bottom door 23 is in a closed position and is attached to the chassis 22 (see FIG. 1) via the living hinge 34. In one embodiment, the base 21 is secured to the housing assembly 20 such that no opening other than when the door 23 is in an open position is greater than about 0.01 inch (0.03 cm), or more preferably no greater than between about 0.01 inch (0.03 cm) to about 0.25 inch (0.64 cm). In another embodiment of the present invention, no opening when the door 23 is closed has a cross section wider than about 0.01 inch (0.03 cm), or more preferably wider than about 0.25 inch (0.64 cm).

Figure 9:
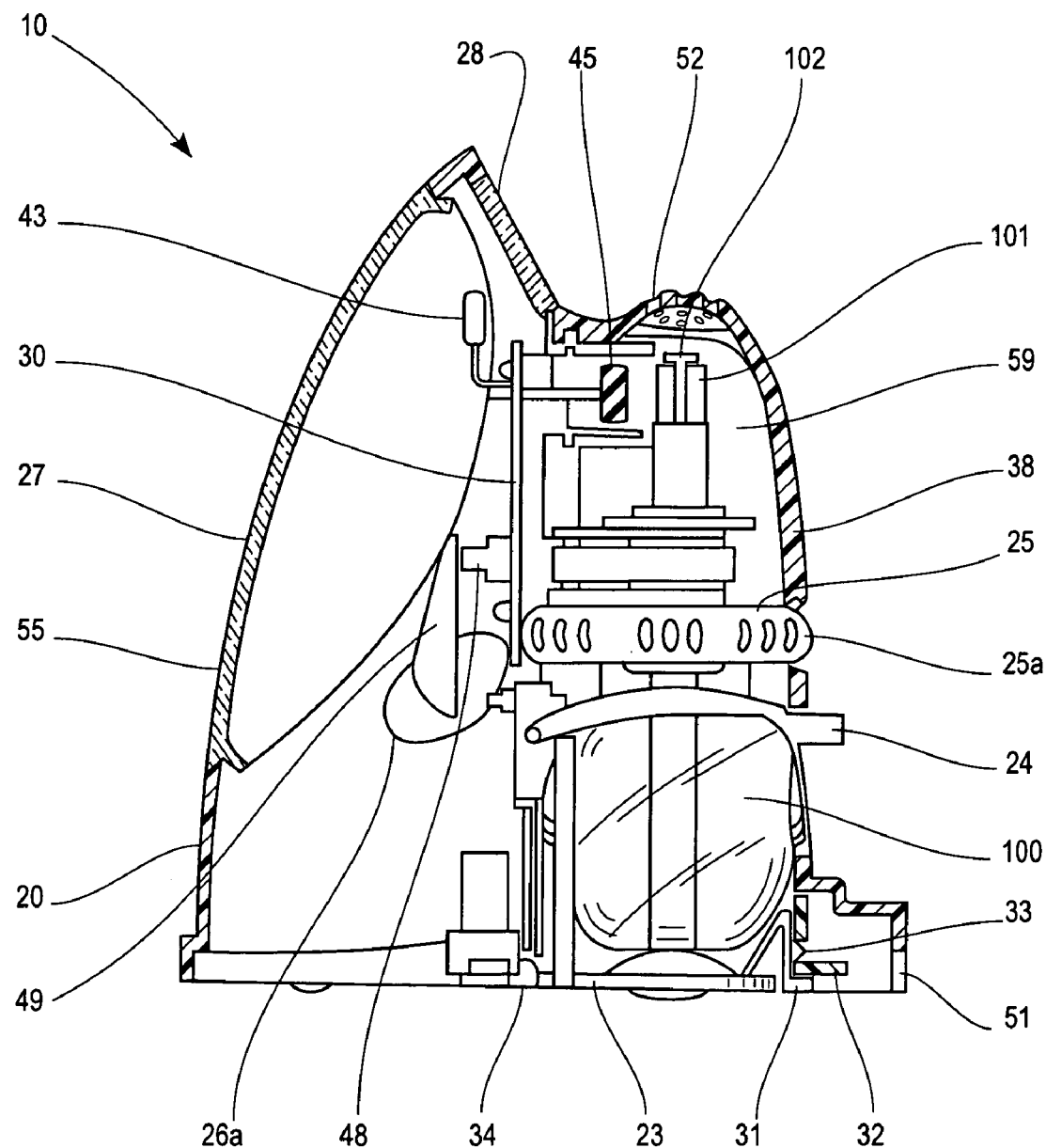
FIG. 9 is a cross-sectional view of an embodiment of FIG. 1 incorporating a container having a wick extending therefrom and taken generally along the lines 9-9 of FIG. 5.
Figure 10:
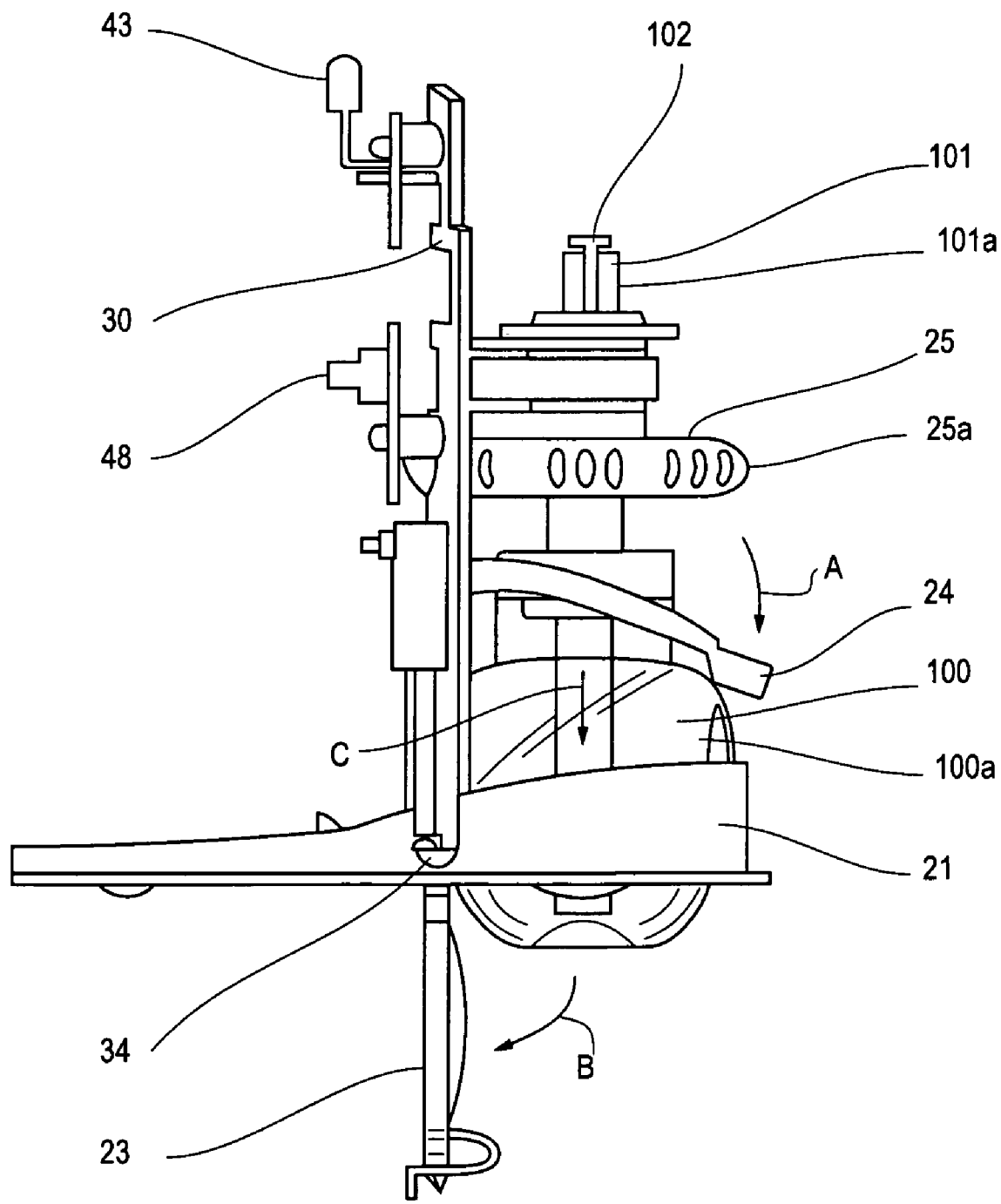
FIG. 10 is a side elevational view of the diffuser of FIG. 1 with the housing omitted, showing the internal electronic and mechanical components of the diffuser.

Inside the housing assembly 20 is an interior compartment 59 for receiving, releasably engaging, and/or retaining a refill bottle or container 100 (see FIGS. 9 and 10). The ejector arm 24 is shown disposed below the wick adjustment mechanism 25 and has an opening 24a to receive the refill bottle or container 100. Top vents 52a may be seen disposed at the top of the interior compartment 59. When the refill bottle 100 is received in the interior compartment 59, the fan-like protrusion 58 disposed on the chassis 22 (see FIG. 1) and positioned below the ejector arm 24 is configured to engage a refill bottle or container and to assist in receiving, releasably engaging, and/or retaining the refill bottle or container in the diffuser 10. The interior compartment 59 may be configured to receive, releasably engage, and/or retain any type of container suitable to contain an active material. Illustrative containers useful in the present invention for holding the active material are those refill units sold under the tradename GLADE®, PLUGINS®, SCENTED OIL®, and/or RAID® brand names ®, by S.C. Johnson & Son, Inc., and those disclosed in, for example, in U.S. Pat. No. 4,849,606.

As shown in FIGS. 9 and 10, a refill bottle or container 100 with a wick 101 extending therefrom is received in an interior compartment 59 of the diffuser 10. A plastic shield or protective cover 102 encloses a portion of the wick 101 to protect the wick from damage as it is inserted into the interior compartment 59. The plastic shield or protective cover 102 may also surround the wick 101 to protect the components of the diffuser 10 from contact with the active material contained in the wick. As seen in FIG. 9, vent openings 52a in the housing 20 are disposed above the wick 101 to provide ventilation to the outside atmosphere. The ejector arm 24 is pivotally mounted and positioned to eject the refill bottle or container 100 from the interior compartment 59. The ejector arm 24 is configured to cantilever over a top portion between a body 100a of the container 100 and an upper portion 101a of the wick 101 of the container when the container is received or being inserted into the interior compartment 59. As shown in FIG. 9, a portion of the ejector arm 24 protrudes from the housing assembly 20 so as to allow engagement with a hand and/or a finger of a user, such that, for example, sufficient pressure may be exerted by the user on the ejector arm 24 and the refill bottle or container 100 to disengage and eject the refill bottle or container from the interior compartment 59. The heater 45 and the adjustment mechanism 25 are positioned to displace the upper portion 101a of the wick 100 toward or away from the heater. In one embodiment the heater 45 is disposed at least 3 inches (7.62 cm) from the opening 31 in the housing assembly 20, such as an opening accessible to a human hand or finger. In one embodiment of the present invention, ejection of the refill bottle or container 100 from the interior compartment 59 is accomplished only by first opening the reclosable door 23. Such a configuration reduces the risk of accidental ejection of the refill bottle or container 100 from the interior compartment 59 during, for example, transport and/or handling of the device. The reclosable door 23 may also be tamper and/or age-specific resistant. For example, a reclosable door 23 may be configured to be resistant to being open by children and/or young adults. In other embodiments, an ejector mechanism, such as the ejector arm 24 as shown in FIGS. 1-10, is configured such that a user must apply enough force by pressing up, down, and/or sideways on the ejector mechanism 24 to open a hatch or cover, such as a reclosable door 23, that encloses a refill bottle or container 100 in an enclosed interior compartment 59 when the hatch or cover is in a closed position, and disengage and eject the refill bottle or container 100 from the interior compartment.

Figure 18:
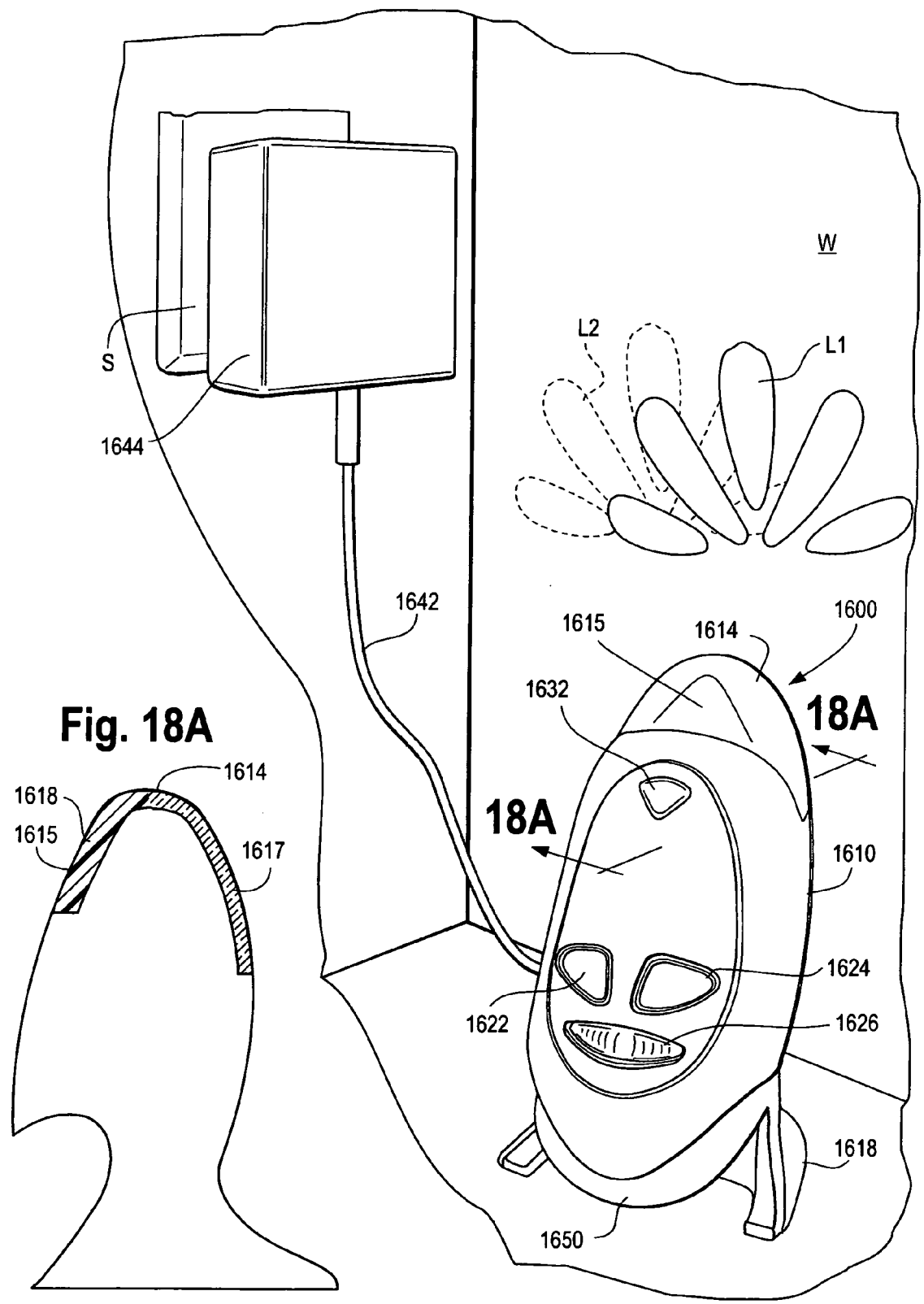
FIG. 18 is an isometric view of another embodiment of a diffuser of the present invention, showing a wall wash projected from the diffuser.
Figure 19:
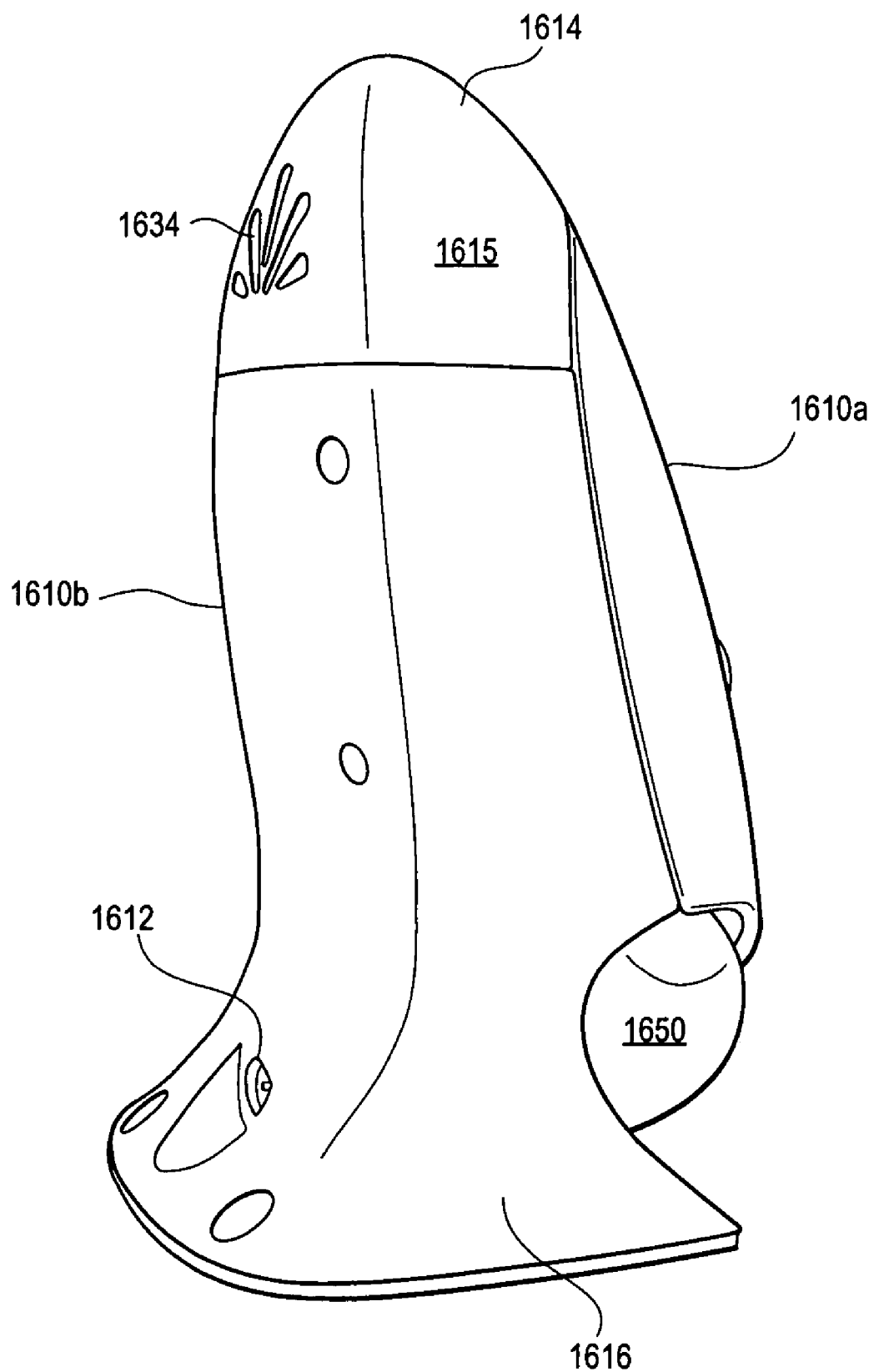
FIG. 19 is an isometric view of the embodiment of FIG. 18.

As shown in FIGS. 18 and 19, a direct-corded diffuser 1601a multi-piece housing 1610 (having a front portion 1610a and a back portion 1610b), a container 1650 of active material, and a heater 45 (shown schematically in FIG. 14) similar to those described above with respect to the above embodiments. Accordingly, details of the construction of those elements are omitted.

In addition, the diffuser 1601 of this embodiment shows a remote-use assembly that supplies electrical energy to the diffuser 1601 from a remote wall socket S. The remote-use assembly of this embodiment comprises a transformer/rectifier 1644, a cord 1642, and a receptacle (not shown) electrically connected to the cord. The transformer/rectifier 1644 includes a wall plug (also not shown), which plugs directly into the wall socket S. The transformer/rectifier 1644 steps down the voltage and rectifies the current (for example, converts approximately 110 volts AC from the wall socket S to about 2-15 volts DC, depending on the desired characteristics and features of the diffuser) from the wall socket S. This stepped-down DC power is then supplied through the cord 1642 to the receptacle, which attaches to a jack or plug 1612 on the back portion 1610b of the housing 1610. This arrangement, using the transformer/rectifier 1644, may be preferred from the safety standpoint, since the voltage supplied to the diffuser 1610 is much lower than that at the wall socket S.

In the diffuser 1601 a base 1616 coupled to the housing 1610 supports the diffuser on a support surface at a location remote from the wall socket S. As shown in FIG. 19, the base 1616 is formed integrally with a back portion 1610b of the housing 1610. However, the configuration of the base 1616 is not important. As long as the base provides a support to hold the diffuser in a desired orientation, it can effectively be formed integrally with any portion of the housing or could be provided as a separate element that is coupled to the housing 1610 to hold the diffuser 1601.

The diffuser 1601 also includes an adjustment mechanism 1626 for varying the rate at which the active material is diffused. The adjustment mechanism 1626 adjusts the diffusion rate by moving a wick (not shown) of the container 1650 towards the heater 45, in accordance with the movement of a dial 1626 by a user. Such a wick adjustment mechanism is described in detail in U.S. Patent Application Publication No. US 2003/0138241 A1. The diffused active material exits the diffuser through a chimney or vent 1632 formed in the top of the housing 1610.

A lighting element (not shown in FIGS. 18 and 19, but shown schematically in FIG. 14) of the diffuser 1601 preferably comprises at least one LED, more preferably a plurality of LED's. The LED(s) are disposed in the housing 1610 beneath a lens 1614 that is constructed as an integral optical element. During operation, light from the LED(s) is emitted from the diffuser through one or more thicker portions 1615 (FIG. 18A) so as to project diffuse light from the thicker portion and to project light from the thinner portions. The embodiment shown in FIG. 19 has a number of windows 1634 formed in a back surface of the cover 1614 and arranged in a fan shape. Additionally or alternatively, the lens 1614 is preferably made of a translucent or transparent material of various thicknesses so that light will be emitted through the entire lens 1614 in a projected and/or diffuse pattern.

The diffuser 1601 shown in FIG. 18 includes a pair of LED's (not shown) which shine through the windows 1634, and preferably also through the lens 1614. Light emitted from the windows 1634 can be projected onto a wall W or other surface to form a lighted display or "wall wash" in the shape of the windows 1634. Since two LED's are used in the illustrated embodiment, two separate wall washes L1 and L2 are projected onto the wall W. Such a wall wash L1, L2 feature is possible by locating the diffuser 1601 a short distance from a wall W or other projecting surface. Further, the wall wash L1, L2 feature may be generally applicable to a wide variety of lighting features. For example, any nightlight or lighted diffuser could be configured to create a wall wash on the wall to generate a decorative display. Moreover, the wall wash L1, L2 could be configured to move, by moving either the lighting element or the window through which the light shines, or varying the color and/or intensity of the lighting element, thereby creating a moving or changing projection. Still further, the shape of the at least one window 1634 could be varied by, for example, providing interchangeable inserts or slides of varying shape, color, opacity, or the like, so as to allow a user to change the projected image by simply changing the insert.

A pair of switches 1622, 1624 is provided on the diffuser 1601. Preferably, these switches control operation of the light source 43. For example, the first switch 1622 is used to select from among a plurality of color programs to change the color of light emitted from the diffuser, and the second switch 1624 is used to control the brightness or intensity of the LED's. The switches 1622, 1624 could also be connected to one or more light controllers, such that when actuated by the respective switch, the light controller controls the color and/or intensity of the LED's. Alternatively, each of the buttons 1622, 1624 could be used to control a different one of the LED's 1690, such that each LED can be separately turned on and off manually by pressing the button associate with that LED. In another alternative, switch 1622 could be used to control operation of the heating element 1608 and switch 1624 could be used to control operation of both of the LED's. Of course any number of different switches could be used to control different functions, depending on the specific configuration of the diffuser.

In embodiments that utilize a heater, an active material useful in the present invention is a material where the diffusion and/or volatilization rate is enhanced by the application of heat. Such active materials include organic and/or synthetic air freshener compositions, insect control compositions (repellants and insecticides), sanitizers, and the like. Suitable examples of air freshener compositions useful in the present invention include those described in, for example, U.S. Pat. No. 4,849,606. Examples of insect control compositions useful in the present invention include those described in, for example, U.S. Pat. No. 6,503,459. Other examples of insect control compositions useful in the present invention include those described in, for example, U.S. Pat. No. 6,337,080. In embodiments that utilize a piezoelectric device, compositions useful in the present invention are described in, for example, U.S. Pat. No. 6,482,863. Scented oils and containers for holding the oils suitable in the present invention include those described in, for example, U.S. Pat. No. 5,647,053. In another embodiment of the present invention, an active material is a volatilizable material such as, for example, a volatile material that vaporizes at or near room temperature, or less than about 266° F. (130° C.), or less than about 149° F. (65° C.), or between about 149° F. (65° C.) and about 266° F. (130° C.), or any volatile material the vaporizes above about room temperature. Volatilizable materials useful in the present invention include, for example, air quality modification agents, pest control agents, and/or allergen control agents. An example of an air quality modification agent includes a volatile material that changes the smell or scent of the air, and includes, for example, perfumes, fragrances, and/or air deodorizers. Pest control agents include, for example, insecticides, insect growth regulators, repellents, and any other volatile material that kills or affects the development, functioning, or behavior of a pest animal, including, for example, insects. The volatilizable material may include, for example, a carrier such as a polymer, a ceramic, and/or clay, or any other material suitable for containing a volatile material for heated volatilization. The volatilizable material may be, for example, a liquid, a gel, a semisolid, or a solid under ambient conditions.

A refill bottle or container useful in the present invention includes conventional bottles, containers, and/or similar devices configured to receive a volatilizable material and optionally hold at least one wick in place. The refill bottle may be made of any desired material including, for example, glass, metal, and/or a plastic material, which is compatible with the material to be vaporized. For example, a refill bottle may be made of polypropylene, BAREX®, ZEONOR® and/or polyethylene terephthalate (PET), and combinations thereof.

A wick of the present invention may be of any desired wick material, such as, for example, a porous/sintered plastics or polymers, such as ultra-density or ultra-high-density polyethylene and polypropylene, bonded fibers, glass sintered fibers, ceramic materials, carbon fibers, sintered carbon, wood, metal foams, compressed wood composites, bundled fibers, woven material fibers, natural fibers, synthetic fibers, and the like.

In embodiments of the present invention, all or a substantial portion of the outside surface of a device that may come in contact with skin contact of a user such as a hand or finger, including, for example, substantially the entire outside surface of a device, does not exceed a temperature of, for example, where a material is a metal, the surface temperature does not exceed about 122° F. (50° C.), or more preferably about 131° F. (55° C.), or more preferably about 140° F. (60° C.), or more preferably about 149° F. (65° C.), or more preferably about 158° F. (70° C.); while a plastic surface does not exceed about 140° F. (60° C.), or more preferably about 167° F. (75° C.), or more preferably about 176° F. (80° C.), or more preferably about 185° F. (85° C.), or more preferably about 230° F. (110° C.), or more preferably about 212° F. (100° C.); and a glass surface does not exceed a temperature of about 131° F. (55° C.), or more preferably about 149° F. (65° C.), or more preferably about 158° F. (70° C.), or more preferably about 167° F. (75° C.), or more preferably about 194° F. (90° C.); and a surface of a polymeric material does not exceed a temperature of about 194° F. (90° C.), or more preferably about 203° F. (95° C.), or more preferably about 257° F. (125° C.), or more preferably about 266° F. (130° C.); while the device is operated at about ambient temperature of, for example, about 77° F. (25° C.), or between about 70° F. (21° C.) to about 86° F. (30° C.).

Different lens thickness 90, 1615 may also be incorporated into an individual lens or various lenses may have different lens thicknesses in the diffuser 10, 1610. For example, in FIG. 9, the front lens 27 is shown as a lens of substantially uniform thickness. In other embodiments, different sections of the lens 28, 1614 are thicker 90, 1615 than other sections, such as section 1617, with the thicker sections 90, 1615 being more opaque such as at 1618 in FIG. 18A to light therefore giving a more diffuse light display and/or projecting a pattern. In some embodiments the diffuser lens 29 of FIG. 1 can be eliminated as shown in FIG. 9 where the front lens 27 is of a thickness and opaqueness that sufficiently diffuses the light emitted from the light source 43 such that the lens is substantially nontransparent and provides, for example, a glowing effect from the emitted light. In other embodiments, the lens can be frosted and/or polished to provide the same effect as increasing the thickness and opacity of the lens including, for example, providing a glowing effect.

Lenses 27, 28, 1614 of the present invention may be made from any suitable material that may transmit an amount of light, including, for example, a transparent or semitransparent material such as, for example, glass, or plastics, and withstand the heat or energy generated by a particular light source 43 and/or heater 45 utilized in a device of the present invention. Illustrative examples of plastics useful in the present invention include polyvinylchloride, ethylene propylene co-polymers, polyamides, polyolefins, styrenic polymers, acrylics, polycarbonates, polymethylpentene, nitrile polymers, cellulose acetate polymers, and/or polyesters. Examples of polyolefins useful in the present invention include polyethylene, polypropylene, blends of these two resins known as polyallomers, and cyclo olefin polymers. Examples of polyamides includes nylon 66, nylon 6 and amorphous nylon. Examples of styrenic polymers include polystyrene, styrene-acrylonitrile copolymers, transparent acrylonitrile-butadiene-styrene copolymers and styrene-butadiene block copolymers. Examples of polyesters include polyethylene terephthalate, copolyesters made with cyclohexanedimethanol and/or isophthalic acid comonomers, polyethylene naphthalate, and their blends. A resin useful in the present invention includes, for example, a metallocene homopolymer polypropylene and may be produced using single-site catalyst. Clarifiers and/or a nucleation additive may also be added to the material to improve clarity. In some embodiments where injection molding and/or thermoforming is utilized to manufacture a lens, the material selected to make the lens has a melt flow rate compatible with the manufacturing technique. For example, a metallocene homopolymer polypropylene that has a melt flow of about 2.3 g/10 min. is suitable for injection molding or thermoforming. The lenses may also be made from standard homopolymer or random copolymer polypropylene resins (made, for example, using multi-site Ziegler-Natta type catalyst) that contain a clarifier and/or a nucleation additive to improve clarity. Illustrative polypropylenes useful in the present invention include:

1. Total 3622M homopolymer polypropylene-clarified, from Total Petrochemicals USA, Inc.;
2. Total 7231M random copolymer polypropylene-clarified, from Total Petrochemicals USA, Inc.;
3. Inspire D118.01 Developmental Performance polypropylene, from Dow Chemical Company;
4. Inspire D404.01 Developmental Performance polypropylene, from Dow Chemical Company;
5. Total M3282MZ metallocene homopolymer polypropylene, from Total Petrochemicals USA;
6. TR-3020-C random copolymer polypropylene-clarified, from Sunoco Chemicals;
7. FT-021-N homopolymer polypropylene-nucleated, from Sunoco Chemicals; and
8. Achieve 1605 metallocene homopolymer polypropylene, from ExxonMobil.

Suitable isotactic polypropylene homopolymers and/or copolymers useful in the present invention include the compounds disclosed in, for example, U.S. Pat. No. 6,727,332, by Demain. Other suitable isotactic polypropylene homopolymers and/or copolymers useful in the present invention include the compounds disclosed in, for example, U.S. Patent Publication No. 2004/0249094, by Demain. Suitable metallocene polypropylene resin compounds useful in the present invention include the material disclosed in, for example, International Publication No. WO 95/30708. Other polyolefins useful in the present invention include polyolefins disclosed in, for example, European Patent Application No. 92870153.1, by Ewen, et al. Still other polyolefins useful in the present invention include those disclosed in, for example, European Patent Application No. 02079921.9, by Razavi. Other transparent or semitransparent resins useful in the present invention include the resins disclosed in, for example, U.S. Pat. No. 6,864,320, by Ogawa, et al. Other suitable materials useful in the present invention include the material disclosed in, for example, U.S. Pat. No. 6,781,761, by Raymond. Still other suitable materials useful in the present invention include the material disclosed in, for example, U.S. Pat. No. 6,824,721, by Albe, et al. Yet other suitable materials useful in the present invention include the material disclosed in, for example, U.S. Pat. No. 6,818,711, by Bauch. Other suitable material useful in the present invention include the compositions disclosed in, for example, U.S. Pat. No. 6,239,216, by Montanari, et al. Nylon and nylon copolymers useful in the present invention include the nylon and nylon copolymers disclosed in, for example, U.S. Pat. No. 6,478,440, by Jaworski et al. Blends of the above materials may also be used in the present invention including, for example, the polypropylene blends disclosed in U.S. Pat. No. 6,407,177, by Shamshoum, et al. Other polypropylene blends useful in the present invention include those disclosed in, for example, U.S. Pat. No. 6,268,062, by DeMuse. Other suitable plastics and blends, mixtures, and/or derivatives thereof useful in the present invention may also be prepared using standard procedures known to those skilled in the art of synthetic organic chemistry and described, for example, by J. March, *Advanced Organic Chemistry; Reactions, Mechanisms and Structure*, 4$^{th}$ Ed. (New York: Wiley-Interscience, 1992); George M. Benedikt, editor, Metallocene Technology in Commercial Applications, (New York: Plastics Design Library, 1999); Cornelia Vasile, editor, Handbook of Polyolefins, 2$^{nd}$ Ed. (New York, Marcel Dekker, Inc., 2000); D. R. Paul & C. B. Bucknall, editors, Polymer Blends, Vol. 2: Performance (New York, Wiley-Interscience, 2000); and Irvin I. Rubin, editor, Handbook of Plastic Materials and Technology, (New York, Wiley-Interscience, 1990).

A consideration in selecting a lens material for use in the present invention is the crystallization properties of the material and the ability to control the crystallization properties such that by varying a lens thickness an area of the lens may appear clear in a thin section and hazy or opaque in thicker regions. Polymers such as polystyrene, polycarbonate, styrene acrylonitrile copolymers (SAN), polyethylene terephthalate (PET) and polyvinyl chloride (PVC) polymers tend to be clear regardless of thickness, but may still be utilized in the present invention be altering a surface of the material to impact light transmittance through the altered surface. Another consideration in selecting the lens material is resistance to solvents, additives, excipients, and/or carriers used in delivering active ingredients. For example, polypropylene is generally resistant to the solvents found in some fragrances useful in the present invention.

Combinations of the above materials may also be used in the present invention, including, for example, polypropylene and polyethylene blends or co-polymers disclosed in U.S. Pat. No. 6,812,286, by Schardl, Jr., et al.

Lenses 27, 28, 1614 of the present invention may also be treated with inks, dyes, and/or pigments to alter the appearance of the lens and/or to adapt the lens for a specific application. For example, in one embodiment the lens is treated with inks and/or other printed indicia to display product identification, advertisements, warnings, decoration, and/or other information. Various techniques known to those skilled in the art can be used to print on the lens, including, for example, screen printing, letterpress, offset, flexographic printing, stipple printing, laser printing, and so forth, and various types of ink can be used, including one and two component inks, oxidatively drying and UV-drying inks, dissolved inks, dispersed inks, and 100% ink systems. The appearance of the lens may also be altered by laminating a dyed film to the lens, applying a pigmented coating to the surface of the lens, and/or including a pigment in one or more of the materials used to make the lens. Both visible and near infrared dyes and pigments may be used, and include, for example, optical brighteners such as dyes that absorb in the UV and fluoresce in the visible region of the color spectrum. Other additional layers that may be added to alter the appearance of the lens include, for example, opacifying (black) layers, diffusing layers, holographic images or holographic diffusers, and metal layers or coatings. Each of these, for example, may be applied directly to one or more surfaces of the lens, and/or may be a component that is laminated to the lens. In addition to the films, coatings, and additives noted above, the lens material of the present invention may also comprise other materials or additives as are known to the art. Such materials include binders, coatings, fillers, compatibilizers, surfactants, antimicrobial agents, foaming agents, reinforcers, heat stabilizers, impact modifiers, plasticizers, viscosity modifiers, and/or other such materials, and combinations thereof. The lens material may also be subjected to various treatments which modify the surfaces of lens, or any portion thereof, to render the surface more conducive to subsequent treatments such as coating, dying, metallizing, and/or lamination. Such treatments include, for example, treatment with primers, such as polyvinylidene chloride, poly(methylmethacrylate), epoxies, and/or aziridines, or through physical priming treatments such as corona, flame, plasma, flash lamp, sputter-etching, e-beam treatments, and/or amorphizing the surface layer to remove crystallinity.

The lenses 27, 28, 1614 of the present invention may also take any desired shape, and may be in a decorative form if so desired. The lenses 27, 28, 1614 may also be convergent or non-convergent depending on the particular application desired. The lenses 27, 28, 1614 may also be constructed with one or more shaped cutouts or windows 1634, through which the light may pass, so as to project images on a wall or other surface L1, L2 (See FIG. 18). Further, while the figures illustrate the invention with the nightlight at the top, it is possible to orient the dispenser with the nightlight at the bottom or to the side.

A diffuser 10, 1601 may include one or more light sources 43 such as LED's, which shine through a window 1634 and/or lenses 27, 28, 1614. Light emitted from the windows 1634 and/or lenses 27, 28, 1614 may be projected onto a wall or other surface to form a lighted display or "wall wash" in the shape of the windows L1, L2. Where multiple LED's are used, multiple and/or separate wall washes may be projected from the diffuser 10. Such a wall wash feature is possible by locating the diffuser 10, 1601 a short distance from a wall or other projecting surface. By using a corded arrangement, the diffuser 10, 1601 may be readily placed in a desired location for viewing by a user, and/or may be positioned at a desired distance from the projecting surface, for example, to adjust the size of the projected image. Alternatively, the wall wash feature could also be applied to a device that plugs directly into a wall socket. In such an arrangement, the light would project from a back surface 38 of the diffuser 10, 1610 onto the wall above, below, to one or more sides and/or around the wall socket. Further, the wall wash feature may be generally applicable to a wide variety of lighting features. For example, any nightlight or lighted diffuser 10, 1610 could be configured to create a wall wash on the wall to generate a decorative display. Moreover, the wall wash may be configured to move, by moving either the lighting element or the window through which the light shines, or varying the color and/or intensity of the lighting element, thereby creating a moving or changing projection. Sill further, the shape of the window could be varied by, for example, providing interchangeable inserts or slides of varying shape, color, opacity, or the like, so as to allow a user to change the projected image by simply changing the insert. Control of the lighting elements may be accomplished by the provision of one or more light controllers to control the color and/or intensity of the LED's, so as to produce a predetermined presentation. In particular, a programmable processor may be used to allow a user to program the operation of light the controller(s) to control at least one of the color and intensity of at least one of the plurality of LED's, to produce a desired presentation, over a set period, for instance.

While the light source 43 shows three LED's with respect to the embodiments shown in FIGS. 1-10, any number of LED's may be used. In addition, the choice of which color LED's to provide may be influenced or dictated by design preferences. The intensity and exact color of the LED's may also be varied by changing the current applied to each diode. When three colors of LED's are used, typically mixtures of red, green, and blue LED's are utilized. In one embodiment, one of each color LED is provided in close proximity to one of each other color. With such an arrangement, the exact color of each diode of the set of three different colors may be adjusted to create a blended color, for example, amber or purple. This blending may be achieved in one embodiment by providing the three diodes in such close proximity that the observer only sees the blend of colored lights, rather than each individual diode. In yet another embodiment, a light diffuser 10, 1601 may be provided to diffuse the light of the three diodes to produce the combined color. In other embodiments, the lights may be projected off a surface to be combined before being viewed by an observer. Light-emitting diodes of a wide array of colors are readily available from lighting manufactures. In embodiments utilizing LED's, the LED's may be positioned on a device to optimize or maximize the transmission and/or projection of light and/or color from the device 10, 1601. For example, where one or more LED's are placed between two lenses 27, 28 such as seen in, for example, FIG. 1, or under one lens 1615 such as seen in, for example, FIG. 18, the LED's are positioned to project a more intense pattern of light through one lens, for example, the back lens 28, and project a more diffuse pattern of light through another lens, for example, the front lens 27, or through different portions of one lens 1615. This may be accomplished in various ways and by way of example, it may be accomplished by having the LED's in-line as shown, or the LED's be arranged in various shapes including, a triangle, a square, a circle, a rectangle, a random pattern, a shape of an object, or any desired shape depending on the light projection pattern, effect, and/or color desired. For example, in one embodiment of the present invention, a triangular arrangement of LED's provides sharper and/or crisper color definition and/or color mixing patterns, while an in-line arrangement provides a more diffuse and/or muted pattern. The LED may also be angled relative to the lenses to take into consideration the light projection pattern of the LED. For example, with a LED that is constructed to project light in a cone-like patter, for example, a reflective cup is positioned at the base of the LED, the LED is pointed or positioned toward a direction where the highest intensity of light is desired. Using FIGS. 1-10 as an example, where the strongest projected light is desired through the back lens 28 of the diffuser 10, the LED's 43 may be tilted at an angle such that the direction of projected light is substantially through the back lens. Illustratively, the LED is tilted toward the back lens 28 at an angle of between about 5° to about 90°, or between about 10° to about 75°, or between about 15° to about 60°, or between about 20° to about 45°, or about 15°, or about 30°, or about 45°, or about 60°, or about 75°, or about 90°, relative to the angle shown in FIG. 1, for example. Also where a LED is configured to project light in a cone-like pattern, the angle that the LED is position may also depend on, for example, the projection of the light boundary along the outline of the cone. For example, and using FIGS. 1-10 again as an example, the LED's 43 may be tilted in an orientation toward the back lens 28 that moves the cone-light boundary off the front lens 27 thereby providing a more diffuse light display on the front lens without the cone-light boundary. Where multiple LED's are utilized, each LED may be independently positioned to achieve, for example, a desired light effect, light pattern, color, and/or color mix.

A light source 43 useful in the present invention may include, for example, a light bulb such as, for example, an incandescent bulb, a fluorescent bulb, and/or a halogen bulb, a LED, a laser diode, a liquid crystal device, a laser, a cathode ray tube, a micromirror device, a digital light processor, a plasma display, and/or any device that emits light of any energy range.

In addition, a diffuser 10, 1601 according to the present invention may include one or more of a "shine-through" feature wherein light from a light source 43 in the diffuser, such as, an LED, shines through a container 100, 1650, containing an active material including, for example, a glass or plastic bottle filled with a translucent or semi-translucent active material, or a "display feature" where the emission of light, fragrance, and/or sound is controlled by a user including in a coordinated manner. Illustratively, at least one LED of a diffuser 10, 1601 of the present invention is positioned such that when the active material is received in the interior compartment, at least one LED "shines through" the active material. In this embodiment, the active material may be a translucent or semi-translucent material, such as a translucent or semi-translucent solid, semi-solid, gaseous, gel, and/or liquid material, such as, for example, a translucent scented oil contained in, for example, a transparent or translucent container so that light may shine through container, such as, for example, a gel cartridge, or other materials that are transmissive to light.

A kit of the present invention may include at least one component of a device of the present invention. In the case of a diffuser 10, for example, the kit may include a housing assembly 20 having an interior compartment 59 for receiving a container 100 having a wick 101, a heater 45, an adjustment mechanism 25 for displacing the upper portion of the wick 101 toward or away from the heater, an electrical connection to transmit power to the diffuser, a light source, and/or one or more permanent, semi-permanent or replaceable lens to project light emitted from the light source. Illustratively, a kit may include an assembled ready-to-use diffuser 10 and a container filled with a volatilized material such as a fragrance. A user then inserts the container into the diffuser 10 and powers up the diffuser. A set of instruction for the user may also be provided to instruct the user on assembly and/or use of the diffuser 10. The instructions may be age specific and provide adequate instructions that are understood by the particular age group. The instructions may include a description of installing, assembly, use, programming, cleaning, maintenance, and other functions of the device. In some embodiments, parts of a device including, for example, the housing assembly 20, the heater 45, the adjustment mechanism 25, the light source 43, and/or the lenses 27, 28 of a diffuser 10, are configured to be removable. Where the lens or lenses 27, 28 are removable, a kit may contain one or more different kinds or types of lenses of, for example, various colors, shapes, and/or patterns, that may be mixed or matched depending on the particular light display desired. A kit may also include one or more stick-on labels 95 (See FIG. 1) that may be attached to the lens or lenses 27, 28 to project a pattern of light from the device. The light source 43 including, for example, a LED, may also be configured to removable and replaced by a user to, for example, provide different lighting effects with different configurations of LED's.

The various components and subassemblies of the diffuser 10, 1601 may be configured to clip or fit snugly together during assembly in a permanent or semi-permanent manner. In such configurations, the assembly reduces the likelihood that a user accidentally damages or gains access to the electrical circuitry contained within. Such subassemblies may be attached together by any means know in the art, including, for example, gluing or cementing the components or subassemblies together by an adhesive, or the components or subassemblies may be of such close tolerance fit as to prevent easy disassembly. Where adhesives are used, the adhesives may also be included in a kit of the present invention for use by a user. In other embodiments, the various components and subassemblies are ultrasonically welded together.

In other embodiments of the present invention, other configurations of light-emitting diodes can be used in a diffuser 10, 1601 depending on the particular light effect that is desired, including, for example, a nightlight, a multicolored display, a color-changing display, a projection display, and/or a shine-through display. For example, a diffuser 10, 1601 of the present invention can include one or more light-emitting diodes and/or one or more light-emitting diode arrays of one or various colors and/or luminosities. One or more of light-emitting diodes may also be used as a low-temperature, low-power light such as, for example, a nightlight, and/or an ornamental display.

Figure 11:
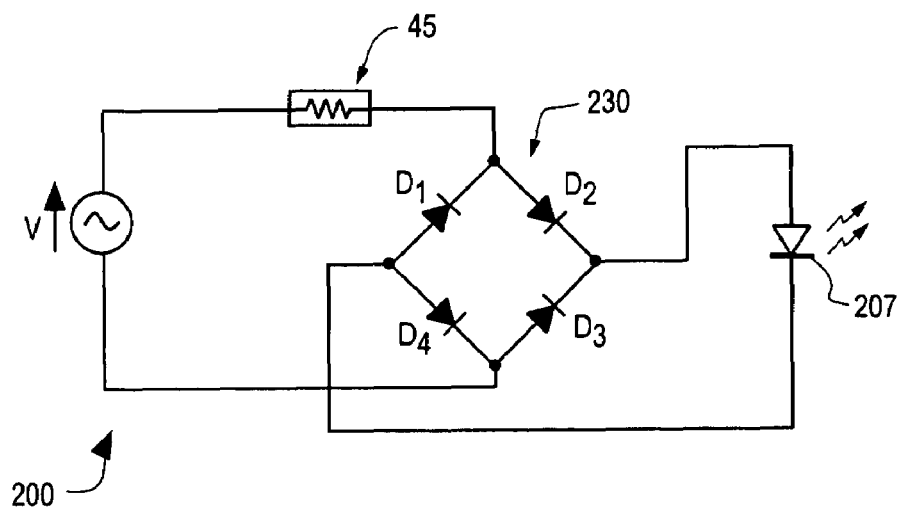
FIG. 11 is a schematic diagram of a first circuit useful in the present invention.
Figure 12:
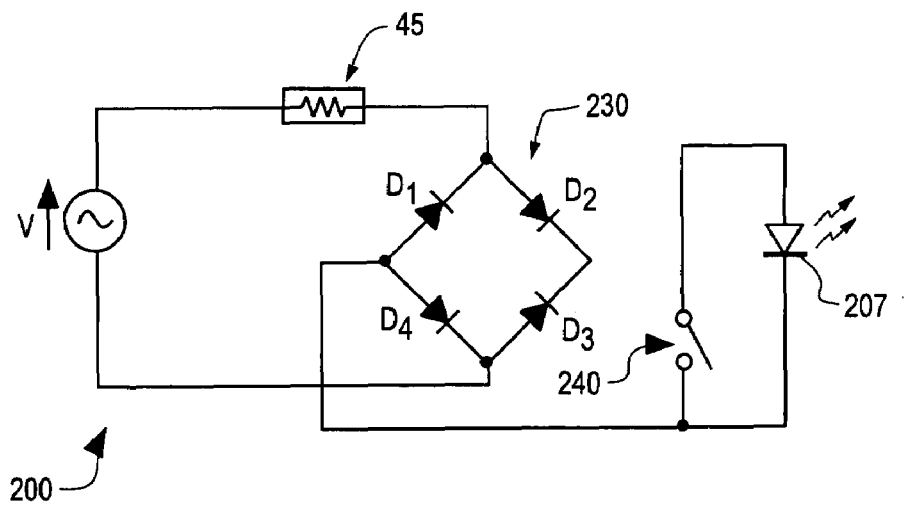
FIG. 12 is a schematic diagram of a second circuit useful in the present invention.
Figure 13:
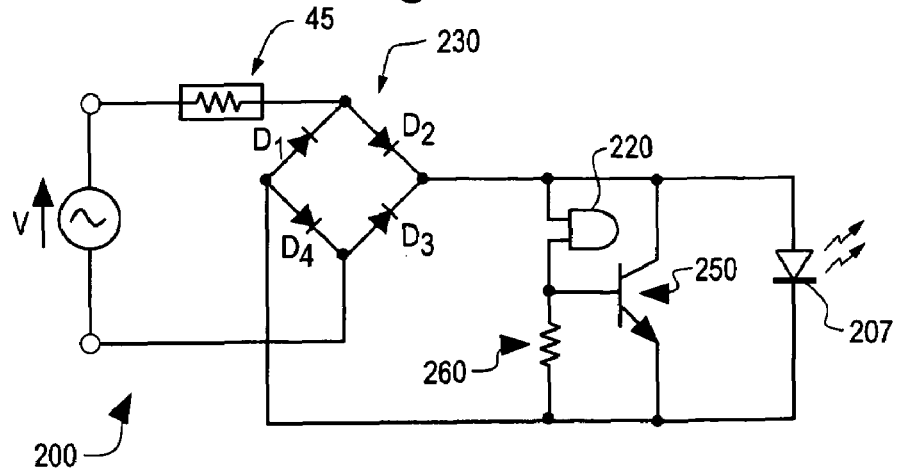
FIG. 13 is a schematic diagram of a third circuit useful in the present invention.

In one embodiment of the present invention, one or more LED's 207 is "always on" whenever power is supplied to a diffuser 10, 1601 and may serve as a nightlight. One such circuit for the "always on" type is shown in FIG. 11. As shown in FIGS. 12 and 13, the LED's 207 that act as a nightlight are controlled by a conventional manual on/off switch 240, or by an automatic circuitry including an ambient light sensor device 220. One such ambient light senor device useful in the present invention is disclosed in, for example, U.S. Pat. No. 6,478,440.

FIG. 11 shows circuit diagram of a circuit 200 useful in the present invention. The circuit 200 of FIG. 11 comprises a heater 45, a bridge circuit 230, and a light-emitting diode lighting element 207. The bridge circuit 230 is of a conventional type, the use of which is well known in the art. The bridge circuit 230 is comprised of four diodes D1-D4 arranged to allow current to flow through the light-emitting diode lighting element 207 in the same direction regardless of the change in polarity of the alternating current from the wall socket. When current from a wall socket is flowing in the direction indicated by the arrow in FIG. 11, the current travels through the heater 45, through diode D2, through the light-emitting diode lighting element 207, and then through diode D4 to complete the circuit. When the current from the wall socket travels in the direction opposite the arrow in FIG. 11 (for example, when the alternating current has the opposite polarity), the current is allowed to travel through diode D3, through the light-emitting diode lighting element 207, though diode D1, and through the heater 45 to complete the circuit.

In another embodiment, instead of a full wave rectification circuit, a half wave rectification circuit may be used. However, the half wave rectification circuit only supplies power to the light-emitting diode lighting element during one polarity of the alternating current waveform, thus, the light-emitting diode lighting element is only on approximately 50% of the time. The other half of the time, the light-emitting diode is off. Accordingly, using a half wave circuit produces a flickering appearance of the light-emitting diode lighting element.

FIG. 12 depicts a circuit diagram of another circuit 200 useful in the present invention. The circuit 200 shown in FIG. 12 is similar to the one shown in FIG. 1, except that a switch 240 is provided to turn the light-emitting diode lighting element 207 on and off. The switch 240 is a manual on/off switch, although any type of switch, manual or automatic, may be used. The circuit diagram of FIG. 12 shows the switch 240 in an open condition, such that the light-emitting diode lighting element 207 is turned on. When the switch 240 is open, the circuit functions in the same manner as the circuit of FIG. 1. When, however, the switch 240 is closed, the current bypasses the light-emitting diode lighting element 207, such that the heater 45 is activated, but the light-emitting diode lighting element 207 is not. With the switch in this closed position, current traveling in the direction of the arrow in FIG. 12 travels through the heater 45, through diode D2, through the switch 240 (which is now closed), and through diode D4 to complete the circuit. When the current from the wall socket travels in the direction opposite the arrow in FIG. 12 (for example, when the alternating current has the opposite polarity), the current is allowed to travel through diode D3, through the switch 240 (which is now closed), though diode D1, and through the heater 45 to complete the circuit.

FIG. 13 depicts a circuit diagram of yet another circuit 200 of the present invention. In this circuit 200, an ambient light sensor device 220 is used to automatically actuate the light-emitting diode lighting element 207 when the light sensor device detects that the surrounding room is dark. The circuit 200 depicted in FIG. 13, is similar to that of FIG. 11, except that it also includes a transistor device 250, a second resistor device 260, and a light sensor 220. In this circuit 200, when the light sensor 220 detects light the light sensor causes the transistor 250 to conduct, such that current bypasses the light-emitting diode lighting element 207 (for example, when current travels in the direction shown by the arrow in FIG. 13, current travels through the heater 45, through diode D2, through transistor 250, and through diode D4 to complete the circuit). However, when the light sensor 220 detects that the room is dark, the transistor 250 turns off, thereby forcing current to flow through the light-emitting diode lighting device 207 following the same path as in the circuit 200 of FIG. 11. Substantial current does not flow through the light sensor 220, because the second resistor 260 has a much higher resistance than does the light-emitting diode lighting device 207.

A current limiting capacitor or resistor could be used with any of the foregoing circuits to limit and/or smooth the current flow in a known manner. As illustrated in FIGS. 11-13, however, a current-limiting capacitor is not required to successfully practice the present invention, since the bridge circuit 230 greatly smoothes the current. Of course, such a current limiting capacitor could be used if desired for particular applications where current fluctuation due to the alternating current is to be minimized, such as where extremely constant light intensity is important. Since no current-limiting capacitor is required, the cost of producing our invention is further reduced, as compared to other existing nightlight devices. If desired, a switch may be added to any suitable point in the circuits of FIGS. 11-13 to that a user can individually control the heater 45 and/or the LED 207.

The electronic circuitry of another embodiment of the present invention is described below with reference to FIG. 14. A brief description of each of these circuits is provided below. However, the drawing figures alone should be sufficient for one of ordinary skill in the art to make and use our invention.

Figure 14:
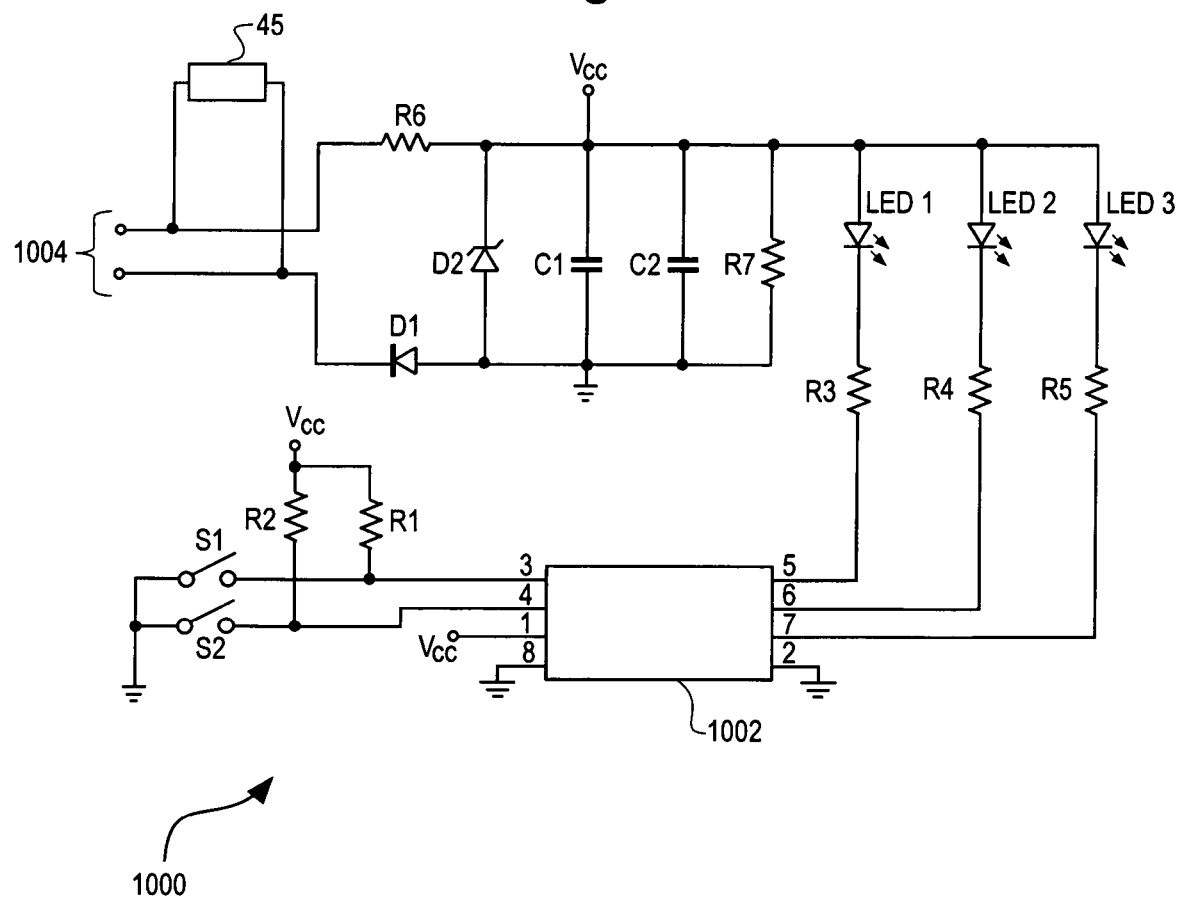
FIG. 14 is a schematic diagram of a circuit according to an embodiment of the present invention.

Referring now to FIG. 14, a circuit 1000 for controlling the heater 45 and light-emitting diodes LED 1, LED 2, LED 3 includes a programmable integrated circuit (PIC) 1002 having pins 1-8. The PIC 1002 may be an 8-bit microcontroller available from Microchip Technology Inc. of Chandler, Ariz., under part number PIC 12C508. If desired, any suitable alternative device may be used, such as a Field-Programmable Gate Array (FPGA), a standard cell integrated circuit, or an Application Specific Integrated Circuit (ASIC) could be used in place of the PIC 1002.

Input voltages $V_{CC}$ and ground are supplied to pins 1 and 8, respectively, of the PIC 1002. The pin 2 of the PIC 1002 is also coupled to ground so that the internal oscillator of the PIC 1002 is utilized to establish the time base of the PIC 1002. Switches S1 and S2 are coupled to pins 3 and 4, respectively, of the PIC 1002, and pull-up resistors R1 and R2 are coupled between the voltage $V_{CC}$ and the pins 3 and 4, respectively. The light-emitting diodes LED 1, LED 2, LED 3 are coupled between a power supply 1004 and first terminals of current limiting resistors R3, R4, and R5, respectively. Second terminals of the resistors R3, R4, and R5 are coupled to pins 5, 6, and 7, respectively, of the PIC 1002.

The power supply 1004 receives power from a transformer (not shown), that converts 120V, 220V, 230V, and/or 240V power into 9 volt AC. The heater 45 is coupled across the output of the transformer. The power supply 1004 includes a diode D1 that half-wave rectifies the incoming AC power, resistor R6, zener diode D2, and capacitors C1 and C2 that together function to provide a stable source of power. An optional further resistor R7 is could across the parallel-connected zener diode D2 and capacitors C1 and C2 to control the intensities of the light-emitting diodes LED 1, LED 2, LED 3. It is understood that other configurations and components may also be used in the present invention to control one or more of the LED's and/or heaters, for example, the above circuit may be configured with one switch to control the LED's if desired.

Figure 15:
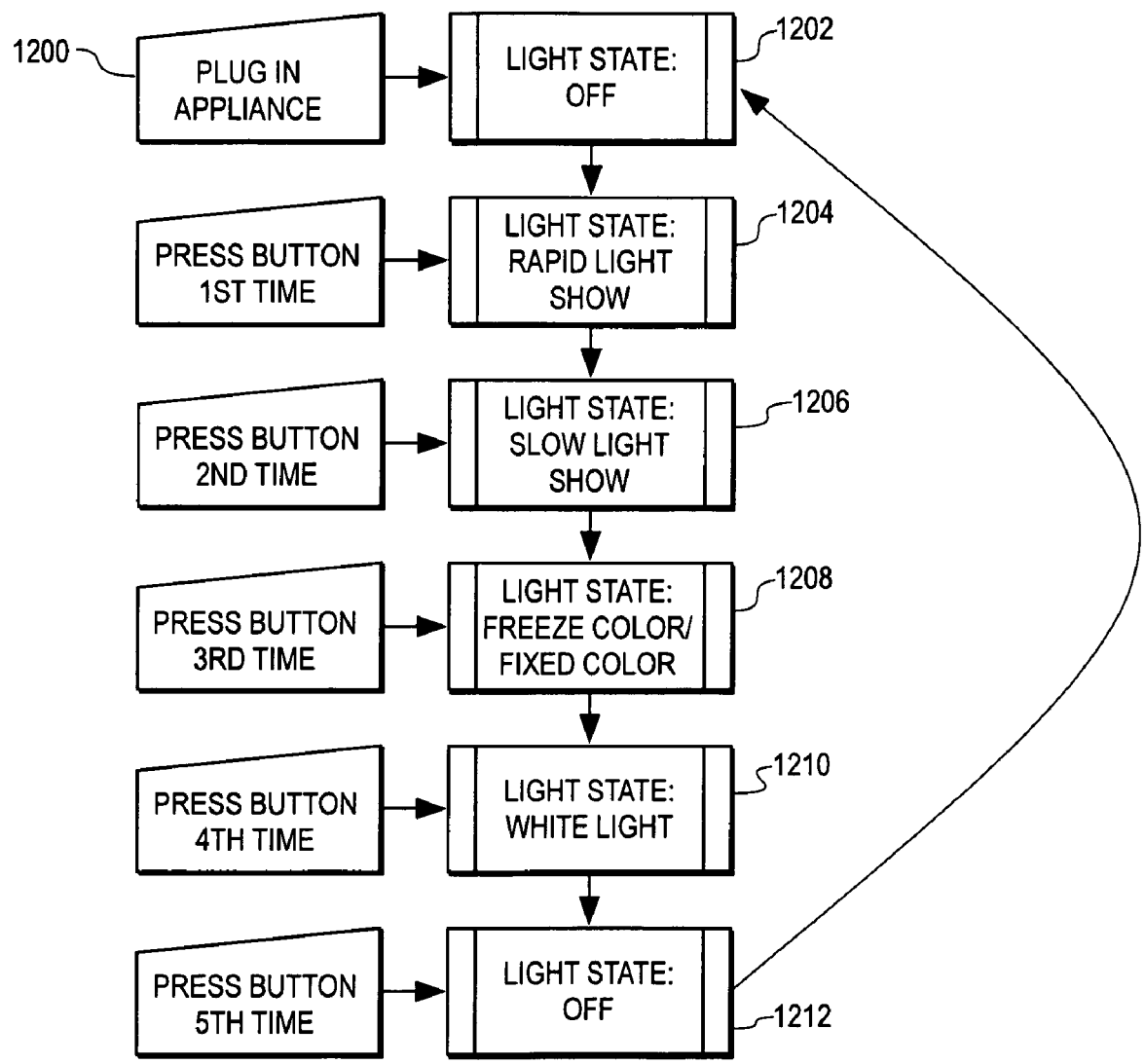
FIG. 15 is a flow chart showing the operation of the embodiment of the present invention illustrated in FIG. 11 according to a first control methodology.

In one embodiment of the present invention, and now referring to FIG. 15, upon initial energizing 1200 a device of the present invention, the light source is off 1202 and the heater is on (not shown). A user interacts with and/or activates a computer source code or software by pressing a set of buttons disposed on the device (for example, see FIGS. 1-9, 26a, 26b) for a preset period of time, for example, between about 20 milliseconds to about 1 second, and controls the function of the lights source. In one configuration, the left button is designated as the light show selection and with an initial depression of the button initiates the light show. Additional depressions of the button progress the light show to the next mode as depicted in FIG. 15. In FIG. 15, Mode 1 1204 is configured to be a light wash or morphing of ever changing colors with high transition speed. Mode 2 1206 is configured to be a light wash or morphing with ever changing colors but with a slow transition speed. The color selection, morphing, and/or transition speed of Modes 1 and 2 1204, 1206 may be defined, for example, by a computer source code or a computer software program such as, for example, a Pulse-Width Modulation technique, a Pulse-Length Modulation technique, and/or a Pulse-Duration Modulation technique. Mode 3 1208 is configured to be a fixed color that matches the color of Mode 2 1206 at the time the button is depressed. Mode 4 1210 is white light and may be an appropriate combination of multiple lights to display white light. Mode 5 1212 is configured to turn the lights off.

Figure 16:
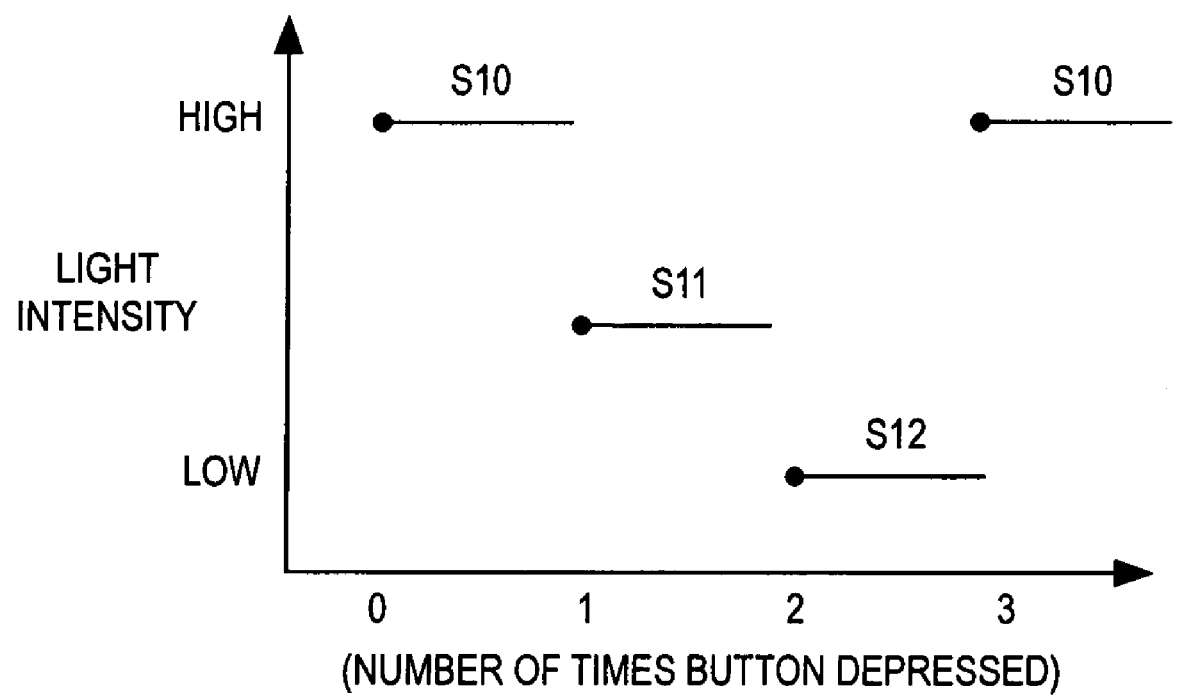
FIG. 16 is a graph showing the operation of the embodiment of FIG. 11 for controlling the light intensity of a lighting source according to the first control methodology.

In this embodiment, the right button is designated as light intensity, and an illustration is provided in FIG. 16. In this embodiment, when the light show is initiated by depressing the left button, the light source is at maximum or 100% intensity S10. Each activation of the button lowers the intensity to the next lower levels S11, S12 with a total of three levels. Upon reaching the lowest setting, pressing the button again returns the light source to the highest intensity level S10 in the same or different mode.

Figure 17:
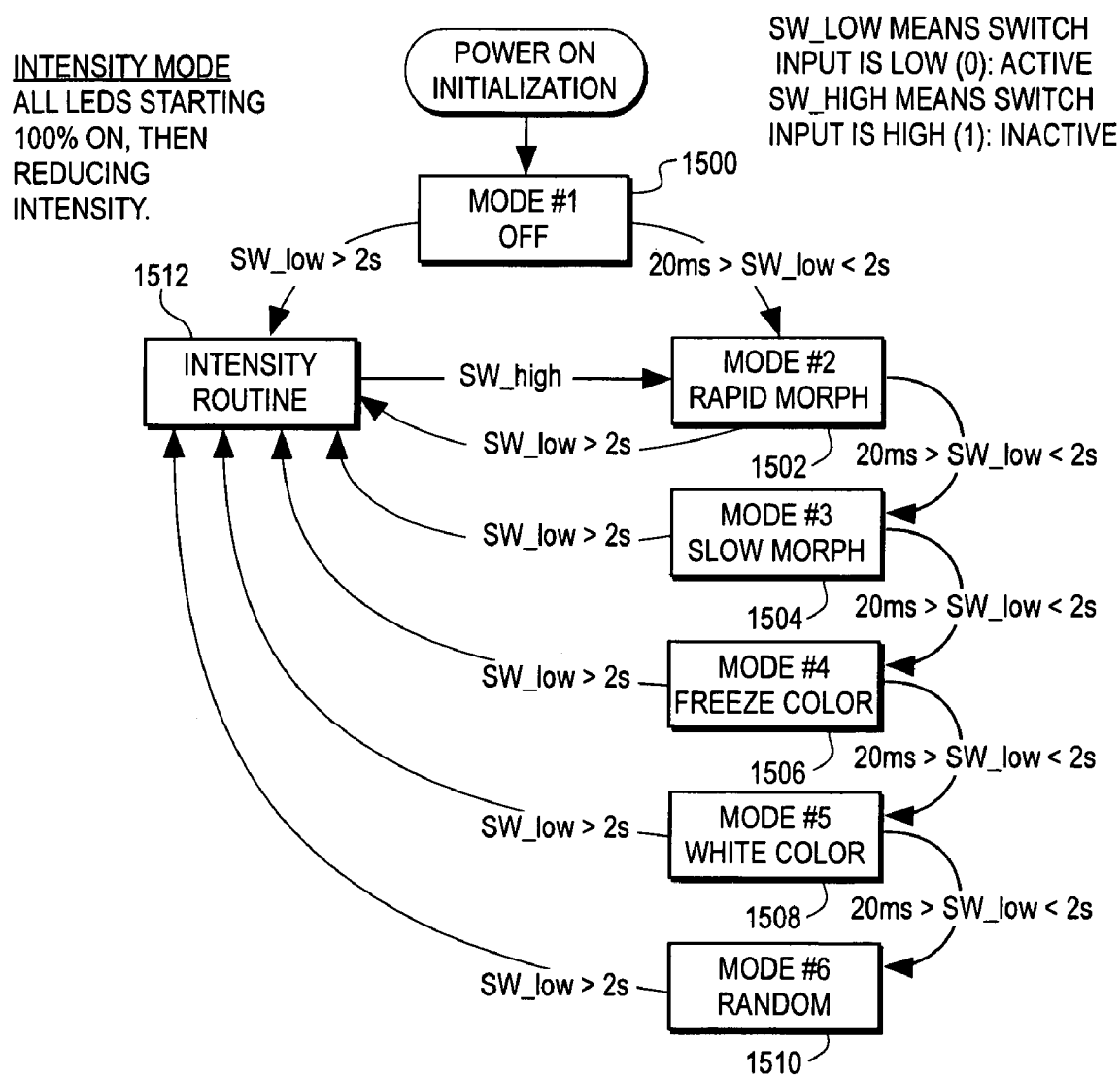
FIG. 17 is a flow chart showing the operation of a modified embodiment of FIG. 11 according to a second control methodology.

In yet another embodiment of the present invention, a device is provided with one button to initiate a light show and to designate light intensity of the lights. For example, in FIG. 17, upon initial energizing a device of the present invention, LED's are off, Mode 1 1500, and by an initial depression of the button for any period of time over 20 milliseconds Mode 2 1502 is entered, which is a light wash or morphing of ever changing colors with high transition speed. Upon entering each mode for the first time in this embodiment, the LED's are at maximum or 100% intensity. Additional depressions of the button from between about 20 milliseconds to about 2 seconds progresses the light show to the next mode as depicted in FIG. 17. As shown in FIG. 17, Mode 3 1504 is a light wash or morphing of ever changing colors with slow transition speed. Mode 4 1506 is a fixed color that matches the color of Mode 3 1504 at the time the button is depressed. Mode 5 1508 is white light and may be an appropriate combination of multiple lights to display white light. Mode 6 1510 is a random mode and is described more fully below. In any of Modes 2 through 6, by depression of the button for a period of time greater than about 2 seconds, the light intensity of the LED's is changed by entering into an intensity routine mode 1512. For example, in one embodiment with each depression of the button greater than about 2 seconds the light intensity of the LED decreases to about 45% of maximum light intensity, then to about 25% of maximum light intensity, and than the LED is turned off. An additional depression of the button greater than about 2 seconds after the LED is turned off returns the LED to maximum or 100% intensity of Mode 2 regardless of the mode at which the LED's were previously in. In another embodiment, the initial intensity for each mode is 100%, and with each depression of the button over about 2 seconds the intensity is decreased a preprogrammed percent of the current intensity level, including, for example, about a 5%, 10%, 15%, 20%, 25%, 50%, or 75% decrease in the current intensity level. In yet another embodiment, the intensity is decreased a random percent of the current intensity until a predetermined intensity is reached. An additional depression of the button may return the light intensity to maximum or 100% intensity in the same mode or in a different mode, or the light intensity increases in the same mode by a preprogrammed percentage increase. In yet another embodiment, with each depression of the button the light intensity is decreased by a preprogrammed amount until the intensity is again set back to 100% in the same or different mode.

Random selection of color using multi-colored light sources may be accomplished by any computer source code or software program known to those skilled in the art. Illustratively, a random mode useful in the present invention with red, green, and blue LED's is shown in Table No. 1, below.

TABLE NO. 1

Random Color Light Display Mode

| Random Number | Light-emitting Diode "ON Mode" = 1 Light-emitting Diode "OFF Mode" = 0 Color of Light-Emitting Diode | | | Color Display |
|---|---|---|---|---|
| | Red | Green | Blue | |
| 1 | 0 | 0 | 1 | Blue |
| 2 | 0 | 1 | 0 | Green |
| 3 | 0 | 1 | 1 | Blue-green |
| 4 | 1 | 0 | 0 | Red |
| 5 | 1 | 0 | 1 | Red-blue |
| 6 | 1 | 1 | 0 | Red-green |
| 7 | 1 | 1 | 1 | White |

In this example, a random number from one to seven is generated by the computer source code or software program and corresponds to a series of 1's and 0's as shown in Table No. 1. A "0" indicates that the LED is in an "OFF Mode" and a "1" indicates that the LED is in an "ON Mode." The various ON/OFF combinations of the three LED's produce a color display as shown in Table No. 1. The duration that the LED is in an ON Mode is determined by a "time on register" software location and controls the amount of time the LED's is on before moving on to the next random color selection. The time a LED is on may be any time range desired, including, for example, from about 0.01 seconds to about 60 seconds or more, or from about 0.05 second to about seconds 30 seconds, or from about 0.1 seconds to about 10 seconds, or about 0.1 seconds to about 5 seconds, or less than about 60 seconds, about 30 seconds, about 15 seconds, about 10 seconds, about 5 seconds, or about 1 second. The source code or computer software program may continuously cycle through the random mode for a preset period of time, and/or a user may input specific or preprogrammed period of time, and/or the cycle may last indefinitely.

Source code other then the Pulse Width Modulating Pulse technique is known to those skilled in the art including, for example, a Code Modulation technique, a Pulse Position Modulation technique, a Pulse Amplitude Modulation technique and/or a Pulse Frequency Modulation technique, and/or other techniques utilizing one or more hardware blocks (standard cells) known to those skilled in the art may also be utilized in present invention to control one or more functions of a light source, including, for example, color selection, morphing, and/or transition speed.

In yet other embodiments, other buttons may be provided to set the duration of, for example, a light presentation and/or fragrance dispersion. The duration may be adjusted by the duration and/or the number of times a button is pushed. For example, one press of the button may initiate a fifteen minute light presentation and/or fragrance dispersion, while an additional press of the button may initiate a thirty-minute duration. Furthermore, one of ordinary skill in the art appreciates that a wide variety of programs may be implemented to produce the desired control over the presentation of, for example, coordinated light, aroma, and/or music, and combinations thereof.

In one embodiment of the present invention, the operation of a diffuser 10 as depicted in FIGS. 1-10 and utilizing the circuitry as depicted in FIG. 14 is as follows. The bottom door 23 of the diffuser 10 is opened and the refill bottle or container 100 is inserted into the interior compartment 59. The recessed portion 58 engages the raised portion or protrusion (not shown) of the refill bottle or container 100 as the refill bottle or container 100 is inserted into the interior compartment 59. The opening 53a in the back housing 38 is also configured to engage the raised portion or protrusion 53 of the inserted refill bottle or container 100 below the ejector arm 24 and is configured to engage the refill bottle. The front surface recess portion or protrusion 53 and the opening 53a in the back housing 38 assist in receiving, releasably engaging, and/or retaining the refill bottle or container 100 in the diffuser 10. The diffuser 10 is plugged into an electrical receptacle of a wall outlet using a cord (not shown). The heater 45 is powered via electricity passing through the cord. Thus activated, the heater 45 generates heat and being in close proximity to a wick 101, heats the wick that absorbs the heat energy thereby causing the active material to be heated and evaporated. The heat energy assists in diffusing the active material into the air through the top vents 52a. A "chimney effect" is created by air entering the bottom vent openings 52b to replace the air exiting the interior compartment 59 due to heat convection. The light source 43 is powered from the electricity supplied to the diffuser 10 and is programmed to be off upon energizing the diffuser. In other embodiments the LED's 43 are always "on," or are controlled by a conventional on/off switch (not shown) or by an automatic circuitry including, for example, an ambient light sensor (not shown).

Additionally, a printed circuit board 30 useful in the present invention may also include one or more controllers, memories, and/or processors for controlling the operation of at least one component of a diffuser 10 including, for example, a LED and/or a heater 45. For example, a light controller circuit may control the color and/or intensity of one or more LED, and a fragrance controller circuit may control the rate of diffusion of the active material by varying the heat emitted from one or more heaters 45. Both controllers may be operated in a coordinated manner, so as to produce a predetermined presentation. In other embodiments, a programmable processor may be used to allow a user to program the operation of the fragrance controller and light controller to control at least one of (i) the rate at which the active material is diffused over the course of the presentation, and (ii) at least one of the color and intensity of at least one of the plurality of LED's, to produce a desired presentation over a set period. Other control options and configuration are described in, for example, PCT/US2004/003533.

INDUSTRIAL APPLICABILITY

The present invention provides apparatuses, methods, kits, and combinations useful for displaying light from a device. For example, a diffuser may be utilized to generate aesthetic lighting displays, such as multicolored displays, color-changing displays, projection displays, shine-through displays, or the like. A diffuser 10 may also be used in locations where the diffuser is directly plugged into, for example, a wall socket, or the diffuser may be corded and be plugged into an electrical power source at a remote location. A diffuser 10 may also provide control over varying emission of light and/or fragrance.

The invention has been described in an illustrative manner, and it is to be understood that the terminology used is intended to be in the nature of description rather than of limitation. All patents and other references cited herein are incorporated by reference in their entirety. Many modifications, equivalents, and variations of the present invention are possible in light of the above teachings, therefore, it is to be understood that within the scope of the appended claims, the invention may be practiced other than as specifically described.

We claim:

1. A diffuser, comprising:
   a housing assembly having a compartment for receiving a container having an active material therein;
   a heating device disposed within the housing assembly;
   an electrical connection to transmit electricity to the diffuser;
   a light source comprising a light-emitting diode;
   a first lens to project light emitted from the light source;
   a second lens to diffuse light emitted from the light source; and
   a third lens disposed between the light source and the second lens to further diffuse light emitted from the light source.

2. The diffuser of claim 1, wherein the first lens is oriented toward at least one of a front, side, top, bottom, or back orientation of the diffuser.

3. The diffuser of claim 1, wherein the first lens comprises a glass, a resin, or a plastic.

4. The diffuser of claim 3, wherein the first lens comprises a plastic comprising polypropylene.

5. The diffuser of claim 1, wherein the first lens diffuses light and projects light.

6. The diffuser of claim 5, wherein the the first lens comprises a single integral optical element.

7. The diffuser of claim 6, wherein the first lens includes a thicker section and a thinner section.

8. The diffuser of claim 7, wherein the thicker section is more opaque to light than the thinner section.

9. The diffuser of claim 1, wherein the first lens includes a portion that is at least one of clear, polished, frosted, colored, etched, painted, and textured.

10. The diffuser of claim 9, wherein the first lens comprises a thicker portion and a thinner portion.

11. The diffuser of claim 10, wherein the thicker portion is more opaque to visible light than the thinner portion.

12. The diffuser of claim 1, wherein the container includes a wick that has an upper portion disposed adjacent the heating device and the diffuser includes an adjustment mechanism for displacing the upper portion of the wick toward or away from the heating device.

13. A method of displaying light and dispensing a fragrance from a diffuser, the method comprising the steps of:
   providing the diffuser, the diffuser including a housing assembly having a reclosable compartment for at least one of receiving, releasably engaging, and retaining a container configured to contain the fragrance; a heating device disposed within the housing assembly at a position proximate to the container; a light source comprising a light-emitting diode; and at least one lens near the light source to display light;
   inserting into the compartment the container having an amount of the fragrance;
   providing a power source to the diffuser; and
   activating the heater and the light source to display the light through the at least one lens and to dispense the fragrance from the diffuser.

14. The method of claim 13, wherein the diffuser comprises at least two lenses.

15. The method of claim 13, wherein light is diffused and projected through the at least one lens.

16. The method of claim 13, wherein the container includes a wick that has one end inserted in fragrance and another end extended therefrom.

17. A multi-clarity lens for displaying light from a device to disperse active material, the multi-clarity lens comprising:
   a polypropylene lens comprising at least one section that is thicker and more opaque to light than at least one other section thereof;
   wherein the device comprises a housing assembly having a reclosable compartment for at least one of receiving, releasably engaging, and retaining a container configured to contain the active material; a heating device disposed within the housing assembly at a position proximate to the container; a light source comprising a light-emitting diode; and the polypropylene lens disposed near the light source to display light.

18. The multi-clarity lens of claim 17, wherein the lens diffuses light and projects light.

19. The multi-clarity lens of claim 17, wherein a section of the polypropylene lens is at least one of clear, polished, frosted, colored, etched, painted, and textured.

20. The multi-clarity lens of claim 17, wherein the container includes a wick that has one end inserted in the active material and another end extended therefrom.

* * * * *